(12) United States Patent
Furukawa et al.

(10) Patent No.: US 12,390,248 B2
(45) Date of Patent: Aug. 19, 2025

(54) ENDOSCOPIC FLEXIBLE TUBE, ENDOSCOPIC MEDICAL APPARATUS, AND ENDOSCOPIC-FLEXIBLE-TUBE-BASE-COVERING MATERIAL

(71) Applicant: FUJIFILM Corporation, Tokyo (JP)

(72) Inventors: Kazushi Furukawa, Kanagawa (JP); Yoshihiro Nakai, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 429 days.

(21) Appl. No.: 18/147,380

(22) Filed: Dec. 28, 2022

(65) Prior Publication Data

US 2023/0157720 A1    May 25, 2023

Related U.S. Application Data

(63) Continuation of application No. PCT/JP2021/024363, filed on Jun. 28, 2021.

(30) Foreign Application Priority Data

Jun. 29, 2020 (JP) .................................. 2020-111757

(51) Int. Cl.
*A61B 17/34* (2006.01)
*A61B 1/00* (2006.01)

(52) U.S. Cl.
CPC ...... *A61B 17/3417* (2013.01); *A61B 1/00002* (2013.01); *A61B 1/00064* (2013.01)

(58) Field of Classification Search
None
See application file for complete search history.

(56) References Cited

U.S. PATENT DOCUMENTS

| | | |
|---|---|---|
| 2009/0198021 A1 | 8/2009 | Ogura et al. |
| 2019/0216292 A1 | 7/2019 | Nakai |
| 2020/0100646 A1 | 4/2020 | Furukawa et al. |
| 2020/0100652 A1 | 4/2020 | Yoshitani et al. |
| 2020/0107697 A1 | 4/2020 | Furukawa et al. |
| 2020/0405918 A1 | 12/2020 | Nakai et al. |

FOREIGN PATENT DOCUMENTS

| | | |
|---|---|---|
| JP | 2004-141487 A | 5/2004 |
| JP | 2009-183467 A | 8/2009 |
| JP | 2015-16261 A | 1/2015 |
| WO | 2018/062330 A1 | 4/2018 |
| WO | 2019/004473 A1 | 1/2019 |
| WO | 2019/004474 A1 | 1/2019 |
| WO | 2019/013243 A1 | 1/2019 |
| WO | 2019/189035 A1 | 10/2019 |

OTHER PUBLICATIONS

International Search Report dated Sep. 7, 2021, issued in International Application No. PCT/JP2021/024363.
Written Opinion dated Sep. 7, 2021, issued in International Application No. PCT/JP2021/024363.
International Preliminary Report on Patentability dated Dec. 13, 2022, issued in International Application No. PCT/JP2021/024363.

*Primary Examiner* — James C Yager
(74) *Attorney, Agent, or Firm* — Sughrue Mion, PLLC

(57) ABSTRACT

An endoscopic flexible tube including a flexible-tube base containing metal as a constituent material, and a cover layer covering an outer periphery of the flexible-tube base, wherein the cover layer includes a polyester having a naphthalene structure and a component having an action of inhibiting a reaction of an active species such as a radical, an endoscopic medical apparatus including the endoscopic flexible tube, and a covering material for the endoscopic flexible-tube base.

7 Claims, 2 Drawing Sheets

ENDOSCOPIC FLEXIBLE TUBE, ENDOSCOPIC MEDICAL APPARATUS, AND ENDOSCOPIC-FLEXIBLE-TUBE-BASE-COVERING MATERIAL

CROSS-REFERENCE TO RELATED APPLICATIONS

This application is a Continuation of PCT International Application No. PCT/JP2021/024363 filed on Jun. 28, 2021, which claims priority under 35 U.S.C. § 119 (a) to Japanese Patent Application No. 2020-111757 filed in Japan on Jun. 29, 2020. Each of the above applications is hereby expressly incorporated by reference, in its entirety, into the present application.

BACKGROUND OF THE INVENTION

1. Field of the Invention

The present invention relates to an endoscopic flexible tube, an endoscopic medical apparatus, and an endoscopic-flexible-tube-base-covering material.

2. Description of the Related Art

The endoscope is a medical apparatus for observing, for example, the body cavity, the alimentary canal, or the esophagus of the patient. Since it is inserted into the body and used, it desirably does not damage internal organs and does not cause pain, uncomfortableness, or the like to the patient. In order to meet such needs, as the flexible tube constituting the insertion section of an endoscope, a spiral tube formed by spirally winding a flexible and bendable metal strip is employed. Furthermore, it is designed such that its periphery is covered with a flexible resin so as not to cause irritation, damage, or the like to linings of the esophagus, the alimentary canal, and the body cavity, for example.

The endoscope for observing the body cavity of the human body is repeatedly used. For this reason, in the endoscope, the flexible tube constituting the insertion section needs to be, after each use, washed and disinfected using a chemical.

For example, JP2009-183467A states that, for an endoscopic flexible tube covered with an outer cover formed of an endoscopic elastomer shaped body provided by cross-linking two or more thermoplastic polyester elastomers, the outer cover is less likely to undergo deterioration due to various chemicals.

WO2019/004473A and WO2019/004474A state that an endoscopic flexible tube covered with a resin layer including a polyester elastomer, a hindered amine compound, and the like is less likely to undergo deterioration of the resin layer due to peracetic acid, and is less likely to undergo, even after being immersed in peracetic acid, peeling of the topcoat layer from the resin layer.

In addition, JP2015-16261A states that, for an endoscopic flexible tube covered with a resin layer including a polyester elastomer and a hindered phenol compound or a hindered amine compound, the resin layer is less likely to undergo deterioration due to peracetic acid.

SUMMARY OF THE INVENTION

In particular, in the cases of insertion into highly susceptible regions such as bronchi, cleanliness of the sterilization grade, which is above the disinfection grade, is required. Thus, endoscopic flexible tubes have come to be required to have high resistance for resisting even repeated sterilization treatments. For sterilization resistance of the endoscopic flexible tubes, recently, a sterilization treatment using ozonated water prepared by dissolving a very small amount of ozone ($O_3$) in water has come to be performed. However, this ozonated water generates a strong active species such as a hydroxy radical and its oxidizing power is stronger than that of hydrogen peroxide gas. Thus, as organic materials that resist the sterilization treatment using ozonated water, just fluororesins are known.

In addition, the outer cover of such an endoscopic flexible tube (the cover layer (for example, a resin layer) of the flexible-tube base)) inevitably contains a very small amount of peroxide due to heating during production steps. In the outer cover, in particular, in the near-surface region of the outer cover, the active species derived from the peroxide decomposes the resin and the like constituting the outer cover. Furthermore, during use of the endoscope, heat generated from, for example, the light source of the illuminator housed within the endoscope, expands the resin and the like constituting the outer cover. The inventors of the present invention performed studies and have found that the decomposition and expansion cause peeling of the topcoat layer from the outer cover. Thus, the endoscopic flexible tube needs to maintain, even after repeated heating, adhesiveness between the outer cover and the topcoat layer.

Under such circumstances, objects of the present invention are to provide an endoscopic flexible tube that exhibits high sterilization resistance against even a strong sterilization treatment using ozonated water and is less likely to undergo, even after repeated heating, peeling of the topcoat layer from the cover layer of the flexible-tube base, and an endoscopic medical apparatus using the endoscopic flexible tube. Another object of the present invention is to provide a base-covering material for the endoscopic flexible tube.

The inventors of the present invention performed thorough studies on how to achieve the above-described objects and, as a result, have found the following: as constituent materials of the outer cover constituting an endoscopic flexible tube, compounds that suppress generation of peroxide or decomposition are combined in a specific mass ratio, and this is used for the cover layer of an endoscopic flexible tube, the cover layer including a polyester having a naphthalene structure, to thereby achieve the above-described objects; thus, they have accomplished the present invention.

The above-described objects have been achieved by the following means.

<1>

An endoscopic flexible tube including: a flexible-tube base containing metal as a constituent material, and a cover layer covering an outer periphery of the flexible-tube base,
  wherein the cover layer includes a component (A) below, a component (B) below, at least one of a component (C) below or a component (D) below, and a polyester having a naphthalene structure,
  in the cover layer, a content of the component (B) below by mass is 0.15 times or more and 1.50 times or less a content of the component (A) below, and
  in the cover layer, a total of contents of the components (C) and (D) below by mass is 0.010 times or more and 0.50 times or less the content of the component (A) below,
component (A): a compound having a structure represented by a general formula (A) below, component (B): at least one of a compound having a structure represented by a general formula (B-1) below, a compound represented by a general formula (B-2) below, or a compound represented by a general formula (B-3) below,
component (C): at least one of a compound represented by a formula (C-1) below, a compound having a structure represented by a general formula (C-2) below, or a compound having a structure represented by a general formula (C-3) below,
component (D): a filler,

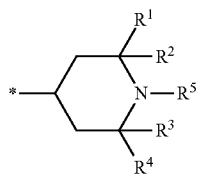

General formula (A)

where $R^1$ to $R^4$ represent a hydrogen atom or an alkyl group having 1 to 12 carbon atoms, $R^5$ represents a hydrogen atom, an alkyl group having 1 to 18 carbon atoms, or —$OR^a$, $R^a$ represents a hydrogen atom or an alkyl group having 1 to 20 carbon atoms, and * represents a bonding site for being incorporated into the compound,

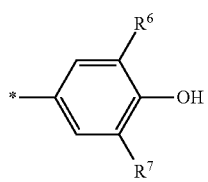

General formula (B-1)

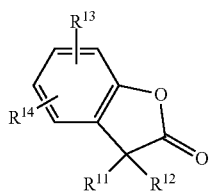

General formula (B-2)

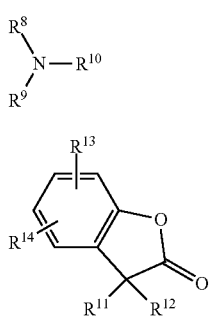

General formula (B-3)

in the general formula (B-1), $R^6$ and $R^7$ represent a hydrogen atom, an alkyl group having 1 to 12 carbon atoms, or an aralkyl group having 7 to 36 carbon atoms, and * represents a bonding site for being incorporated into the compound,
in the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group, $R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^8$ and $R^9$, $R^9$ and $R^{10}$, or $R^8$ and $R^{10}$ may be linked together to form a five- to seven-membered ring without forming a 2,2,6,6-tetraalkylpiperidine skeleton, with the proviso that $R^8$ and $R^9$ are not simultaneously hydrogen atoms, and $R^8$ and $R^9$ have 7 or more carbon atoms in total,
in the general formula (B-3), $R^{11}$ to $R^{14}$ represent a hydrogen atom, an alkyl group having 1 to 20 carbon atoms, or an aryl group having 6 to 15 carbon atoms,

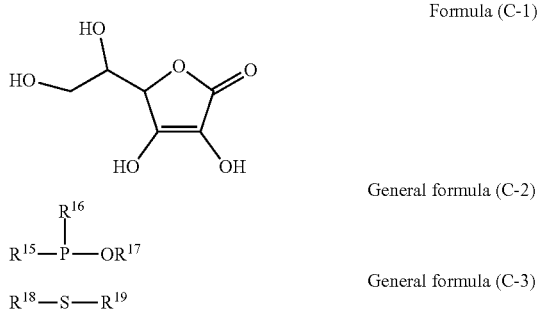

Formula (C-1)

General formula (C-2)

General formula (C-3)

in the general formula (C-2), $R^{15}$ and $R^{16}$ represent an alkyl group, an aryl group, an alkoxy group, an aryloxy group, or a halogen atom, and $R^{17}$ represents an alkyl group or an aryl group, and
in the general formula (C-3), $R^{18}$ and $R^{19}$ represent an alkyl group.

<2>
The endoscopic flexible tube according to <1>, wherein the component (A) includes at least one of a compound represented by a general formula (a-1) below or a compound having a constituent component represented by a general formula (a-2) below,

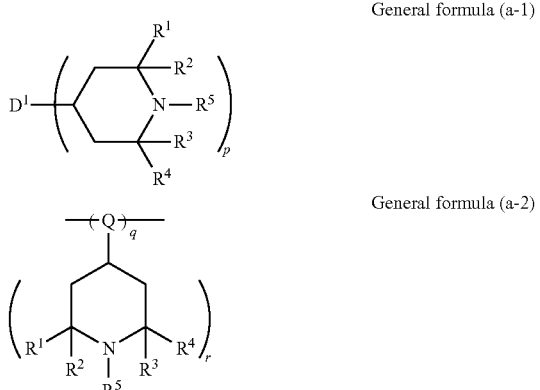

General formula (a-1)

General formula (a-2)

where $R^1$ to $R^5$ respectively have the same definitions as $R^1$ to $R^5$ of the general formula (A), p is an integer of 2 or more, $D^1$ represents a p-valent linking group, q represents a positive integer, Q represents an r+2-valent linking group, and r is 1 or 2.

<3>
The endoscopic flexible tube according to <1> or <2>, wherein the compound having the structure represented by the general formula (B-1) includes at least one of a compound represented by a general formula (b-1) below or a compound represented by a general formula (b-2) below, General formula (b-1)

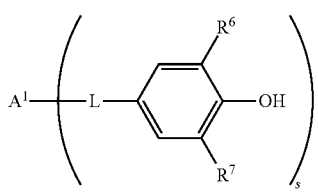

General formula (b-2)

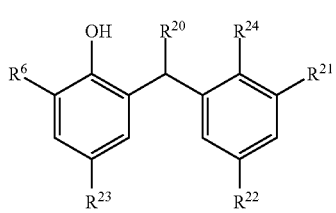

where $R^6$ and $R^7$ respectively have the same definitions as $R^6$ and $R^7$ of the general formula (B-1), L represents a single bond or a divalent linking group, s is an integer of 2 to 4, $A^1$ represents a di- to tetra-valent linking group, $R^{20}$ to $R^{23}$ have the same definitions as $R^6$, and $R^{24}$ represents a reactive organic substituent.

<4>
The endoscopic flexible tube according to any one of <1> to <3>, wherein the component (D) includes carbon black.
<5>
The endoscopic flexible tube according to any one of <1> to <4>, including a topcoat layer.
<6>
An endoscopic medical apparatus including the endoscopic flexible tube according to any one of <1> to <5>.
<7>
An endoscopic-flexible-tube-base-covering material including: a component (A) below, a component (B) below, at least one of a component (C) below or a component (D) below, and a polyester having a naphthalene structure,
  wherein, in the material, a content of the component (B) below by mass is 0.15 times or more and 1.50 times or less a content of the component (A) below, and
  in the material, a total of contents of the components (C) and (D) below by mass is 0.010 times or more and 0.50 times or less the content of the component (A) below,
component (A): a compound having a structure represented by a general formula (A) below,
component (B): at least one of a compound having a structure represented by a general formula (B-1) below, a compound represented by a general formula (B-2) below, or a compound represented by a general formula (B-3) below,
component (C): at least one of a compound represented by a formula (C-1) below, a compound having a structure represented by a general formula (C-2) below, or a compound having a structure represented by a general formula (C-3) below,
component (D): a filler, General formula (A)

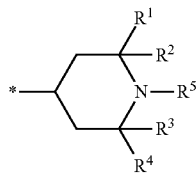

where $R^1$ to $R^4$ represent a hydrogen atom or an alkyl group having 1 to 12 carbon atoms, $R^5$ represents a hydrogen atom, an alkyl group having 1 to 18 carbon atoms, or $-OR^a$, $R^a$ represents a hydrogen atom or an alkyl group having 1 to 20 carbon atoms, and * represents a bonding site for being incorporated into the compound, General formula (B-1)

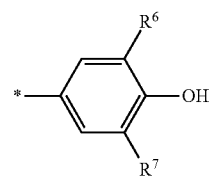

General formula (B-2)

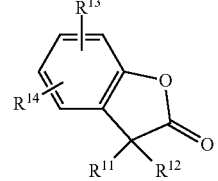

General formula (B-3)

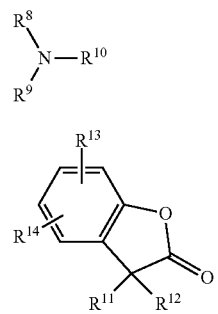

in the general formula (B-1), $R^6$ and $R^7$ represent a hydrogen atom, an alkyl group having 1 to 12 carbon atoms, or an aralkyl group having 7 to 36 carbon atoms, and * represents a bonding site for being incorporated into the compound, in the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group, $R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^8$ and $R^9$, $R^9$ and $R^{10}$, or $R^8$ and $R^{10}$ may be linked together to form a five- to seven-membered ring without forming a 2,2,6,6-tetraalkylpiperidine skeleton, with the proviso that $R^8$ and $R^9$ are not simultaneously hydrogen atoms, and $R^8$ and $R^9$ have 7 or more carbon atoms in total, in the general formula (B-3), $R^{11}$ to $R^{14}$ represent a hydrogen atom, an alkyl group having 1 to 20 carbon atoms, or an aryl group having 6 to 15 carbon atoms, Formula (C-1)

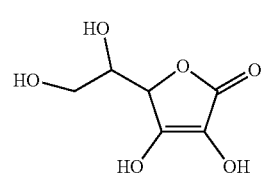

General formula (C-2)

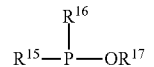

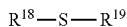
General formula (C-3)

in the general formula (C-2), $R^{15}$ and $R^{16}$ represent an alkyl group, an aryl group, an alkoxy group, an aryloxy group, or a halogen atom, and $R^{17}$ represents an alkyl group or an aryl group, and in the general formula (C-3), $R^{18}$ and $R^{19}$ represent an alkyl group.

In this Specification, in a case where there are a plurality of substituents, linking groups, or the like (hereafter, referred to as substituents etc.) denoted by specific symbols, or in a case where a plurality of substituents etc. are simultaneously or individually defined, in each case, the substituents etc. may be the same or different. When a plurality of substituents etc. are adjacent to each other, they may be linked together or fused together to form a ring, which is not necessarily described.

In this Specification, substituents that are not clearly described in terms of being substituted or unsubstituted (the same applies to linking groups) are intended that they may have appropriate substituents as long as intended advantages are provided. The same applies to compounds that are not clearly described in terms of being substituted or unsubstituted.

In this Specification, when the number of the carbon atoms of a group is defined, the number of the carbon atoms means the number of the carbon atoms of the whole group. In other words, when this group has a form further having a substituent, the number of the carbon atoms means that of the whole structure including this substituent.

In this Specification, "a value 'to' another value" used is intended to include the value and the other value as the lower-limit value and the upper-limit value.

An endoscopic flexible tube according to the present invention exhibits high sterilization resistance against even a strong sterilization treatment using ozonated water and is less likely to undergo, even after repeated heating, peeling of the topcoat layer from the cover layer of the flexible-tube base. An endoscopic medical apparatus according to the present invention is an apparatus that includes the above-described endoscopic flexible tube having good properties. An endoscopic-flexible-tube-base-covering material according to the present invention is suitably used for covering the base of an endoscopic flexible tube according to the present invention.

DESCRIPTION OF THE PREFERRED EMBODIMENTS

Endoscopic Flexible Tube

Figure 1:
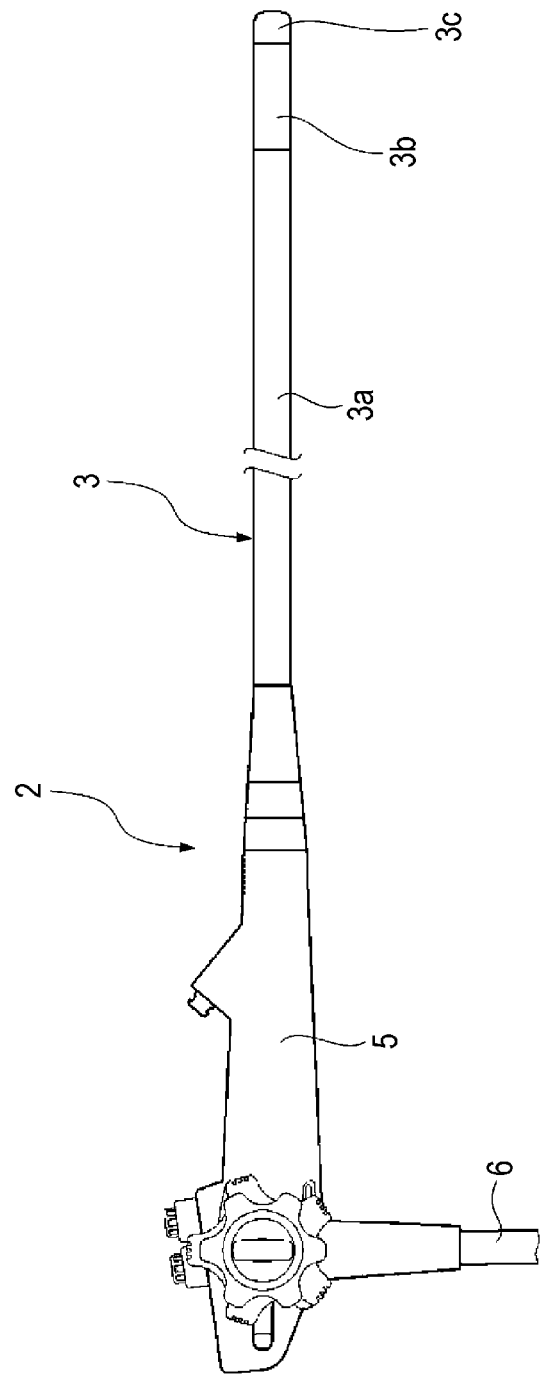
FIG. 1 is an external view illustrating the configuration of an electronic endoscope.

An endoscopic flexible tube according to the present invention (hereafter, the endoscopic flexible tube may also be simply referred to as "flexible tube") includes a flexible-tube base containing metal as a constituent material, and a cover layer covering an outer periphery of the flexible-tube base, wherein the cover layer includes a component (A) below, a component (B) below, at least one of a component (C) below or a component (D) below, and a polyester having a naphthalene structure, in the cover layer, a content of the component (B) below by mass is 0.15 times or more and 1.50 times or less a content of the component (A) below, and in the cover layer, a total of contents of the components (C) and (D) below by mass is 0.010 times or more and 0.50 times or less the content of the component (A) below, component (A): a compound having a structure represented by a general formula (A) below, component (B): at least one of a compound having a structure represented by a general formula (B-1) below, a compound represented by a general formula (B-2) below, or a compound represented by a general formula (B-3) below, component (C): at least one of a compound represented by a formula (C-1) below, a compound having a structure represented by a general formula (C-2) below, or a compound having a structure represented by a general formula (C-3) below, component (D): a filler,

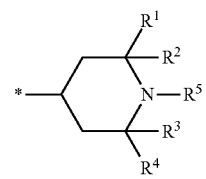
General formula (A)

where $R^1$ to $R^4$ represent a hydrogen atom or an alkyl group having 1 to 12 carbon atoms, $R^5$ represents a hydrogen atom, an alkyl group having 1 to 18 carbon atoms, or —$OR^a$, $R^a$ represents a hydrogen atom or an alkyl group having 1 to 20 carbon atoms, and * represents a bonding site in the compound,

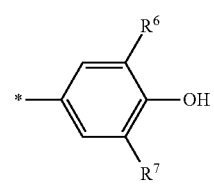
General formula (B-1)

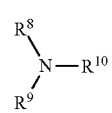
General formula (B-2)

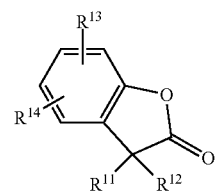
General formula (B-3)

in the general formula (B-1), $R^6$ and $R^7$ represent a hydrogen atom, an alkyl group having 1 to 12 carbon atoms, or an aralkyl group having 7 to 36 carbon atoms, and * represents a bonding site in the compound, in the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group, $R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^8$ and $R^9$, $R^9$ and $R^{10}$, or $R^8$ and $R^{10}$ may be linked together to form a five- to seven-membered ring without forming a 2,2,6,6-tetraalkylpiperidine skeleton, with the proviso that $R^8$ and $R^9$ are not simultaneously hydrogen atoms, and $R^8$ and $R^9$ have 7 or more carbon atoms in total, in the general formula (B-3), $R^{11}$ to $R^{14}$ represent a hydrogen atom, an alkyl group having 1 to 20 carbon atoms, or an aryl group having 6 to 15 carbon atoms,

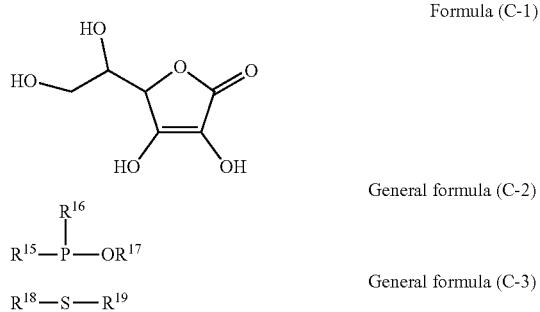

Formula (C-1)

General formula (C-2)

General formula (C-3)

in the general formula (C-2), $R^{15}$ and $R^{16}$ represent an alkyl group, an aryl group, an alkoxy group, an aryloxy group, or a halogen atom, and $R^{17}$ represents an alkyl group or an aryl group, and in the general formula (C-3), $R^{18}$ and $R^{19}$ represent an alkyl group.

In a flexible tube according to the present invention, the cover layer may be a single layer or may be plural layers constituted by layers different from each other in composition (plural layers different from each other in compositional ratio of the constituent dicarboxylic acid component or diol component). The cover layer is preferably a single layer. A flexible tube according to the present invention may have, on the outside of the cover layer, a topcoat layer.

The constituent component of the topcoat layer is not particularly limited and examples applicable include urethane coating materials, acrylic coating materials, fluoro coating materials, silicone coating materials, epoxy coating materials, and polyester coating materials. From the viewpoint of adhesiveness to the cover layer and sterilization resistance, preferred are urethane coating materials, acrylic coating materials, and fluoro coating materials. The topcoat layer may be formed by standard procedures, and may be formed, for example, in the following manner: a solution in which raw materials of the components constituting the topcoat layer are dissolved and a curing agent is contained as needed, is cured. The curing treatment may be performed by, for example, heating at 60 to 200° C.

The main purpose for using the topcoat layer is to protect and to impart glossiness and lubricity to the surface of the flexible tube, and to improve sterilization resistance. Thus, the topcoat layer preferably has a high elastic modulus, a smooth surface, and high sterilization resistance. The topcoat layer alone has a storage elastic modulus E' of preferably 1 MPa or more, more preferably 5 MPa or more, particularly preferably 10 MPa or more. On the other hand, the storage elastic modulus E' is preferably 1 GPa or less, more preferably 500 MPa or less, particularly preferably 300 MPa or less. When the storage elastic modulus E' is set to such a lower-limit value or more, the topcoat has a further improved surface protection function; when the storage elastic modulus E' is set to such an upper-limit value or less, the resultant flexible tube has further improved flexibility.

A flexible tube according to the present invention exhibits high sterilization resistance against even a strong sterilization treatment using ozonated water, and is less likely to undergo, even after repeated heating, peeling of the topcoat layer from the cover layer of the flexible-tube base (high peeling resistance). The reason for this is not clarified, but is inferred as follows.

The polyester having a naphthalene structure inferentially exhibits, due to the magnitude of the molecular area of the naphthalene structure, a barrier function that inhibits transfer and permeation of active species such as a hydroxy radical and a radical derived from peroxide, into the cover layer. In addition, due to the π-π interaction, hydrogen bonds, and the like, in the cover layer, polyester molecules relatively strongly adhere together inferentially. On the other hand, the components (A) to (D) are included, in the cover layer, in specific contents (mass), so that, for example, reactions between the components are suppressed and entry of moisture and the like into the cover layer is inhibited, to thereby effectively exhibit, for example, the action of suppressing generation of peroxide itself, the action of suppressing generation of active species from peroxide, or the action of deactivating active species inferentially. In other words, properties based on the specific structure of the polyester and the actions of the components (A) to (D) closely relate to each other, to suppress thermal expansion of the cover layer and decomposition of the polyester due to active species (in particular, decomposition of the polyester in the topcoat-layer-side region of the cover layer), so that a flexible tube according to the present invention has high ozonated-water resistance and high peeling resistance inferentially.

Flexible-Tube Base

The flexible tube has a flexible-tube base containing metal as a constituent material.

Figure 2:
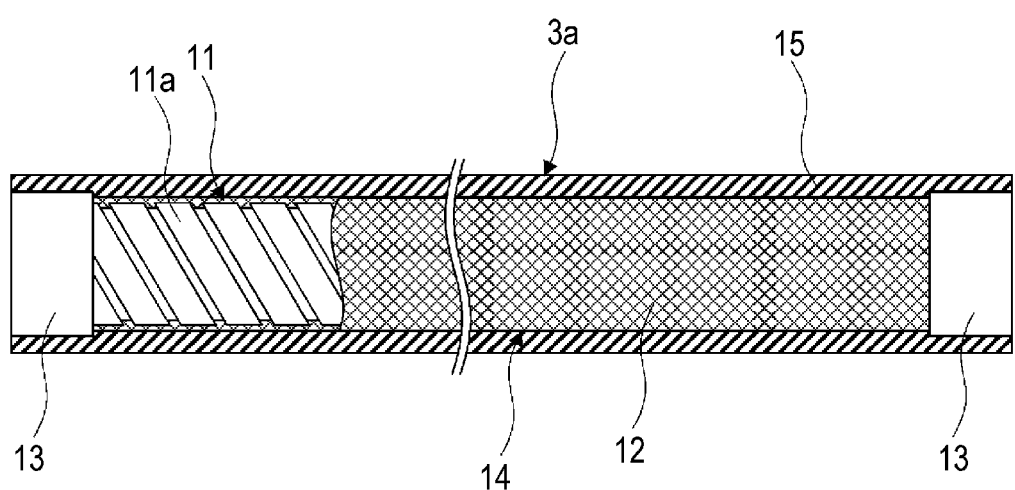
FIG. 2 is a partial sectional view illustrating the schematic configuration of an endoscopic flexible tube.

As illustrated in FIG. 2, a flexible-tube base 14 preferably has the following form: a spiral tube 11, which is disposed on the innermost side and formed by spirally winding a metal strip 11a, is covered with a sleeve-shaped mesh body 12 formed by knitting metal wires; both ends of the spiral tube 11 are fitted with metal caps 13. The constituent metal of the flexible-tube base 14 preferably, in order to prevent corrosion, has a surface having been subjected to a passivation treatment. In other words, the flexible-tube base 14 preferably has an outer periphery (surface) having a passivation film. This passivation treatment can be performed by standard procedures. For example, immersion into a solution including a strong oxidizing agent such as nitric acid, heating in the air (oxygen) or in water (water vapor), or anodic oxidation in a solution including an oxidizing agent can be performed, to thereby form a passivation film on the surface of the metal.

The constituent metal of the flexible-tube base 14 is preferably stainless steel. The surface of stainless steel is ordinarily in a state in which chromium and oxygen ($O_2$) are bonded to form a passivation film. However, even when, as the constituent material of the flexible-tube base 14, stainless steel is used, in order to form a passivation film more uniformly over the whole surface of stainless steel with more certainty, the stainless steel is preferably subjected to the above-described passivation treatment.

Cover Layer

In the present invention, as described above, the cover layer includes the component (A), the component (B), at least one of the component (C) or the component (D), and a polyester having a naphthalene structure. Hereinafter, these components will be described.

Component (A)

The component (A) is a compound having a structure represented by the following general formula (A).

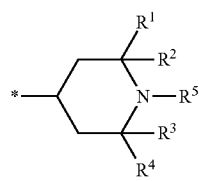

General formula (A)

In the general formula (A), $R^1$ to $R^4$ represent a hydrogen atom or an alkyl group having 1 to 12 carbon atoms (preferably 1 to 8 carbon atoms, more preferably 1 to 5 carbon atoms). Specific examples of such alkyl groups represented by $R^1$ to $R^4$ include methyl, ethyl, n-butyl, isopropyl, s-butyl, t-butyl, t-pentyl, t-hexyl, and t-octyl. $R^1$ to $R^4$ are preferably a primary (linear) alkyl group; more preferably, $R^1$ to $R^4$ are each a primary (linear) alkyl group (particularly preferably a methyl group).

In the general formula (A), $R^5$ represents a hydrogen atom, an alkyl group having 1 to 18 carbon atoms (preferably 1 to 10 carbon atoms, more preferably 1 to 5 carbon atoms, still more preferably 1 to 3 carbon atoms, yet more preferably 1 or 2 carbon atoms), or —$OR^a$; $R^a$ represents a hydrogen atom or a linear, branched, or cyclic alkyl group having 1 to 20 carbon atoms (preferably 1 to 12 carbon atoms). In particular, $R^5$ is preferably a hydrogen atom from the viewpoint of providing higher sterilization resistance.

In the general formula (A), * represents the bonding site in the compound.

The component (A) preferably includes at least one of a compound represented by a general formula (a-1) below or a compound having a constituent component (preferably a repeating unit) represented by a general formula (a-2) below. In the component (A), the total of the contents of the compound represented by the general formula (a-1) below and the compound having a constituent component represented by the general formula (a-2) below is not particularly limited, and is, for example, preferably 50 mass % or more, more preferably 80 mass % or more, still more preferably 90 mass % or more, or may be 100 mass %.

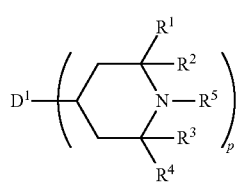

General formula (a-1)

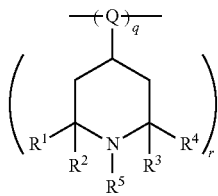

General formula (a-2)

In the formulas, $R^1$ to $R^5$ respectively have the same definitions and preferred examples as $R^1$ to $R^5$ in the general formula (A). p represents an integer of 2 or more (preferably an integer of 2 to 10), and $D^1$ represents a p-valent linking group. r represents 1 or 2. q represents a positive integer and is preferably in ranges of values of the degree of polymerization described later. Q represents an r+2-valent linking group. Examples of Q include a group including an aromatic hydrocarbon group, a group including an imino group ($NR^N$), and a group including a triazine linking group. Specific examples of $R^N$ include a hydrogen atom, an alkyl group having 1 to 20 carbon atoms, and the piperidyl-group-containing group represented by the general formula (A).

The linking group represented by $D^1$ has a molecular weight of preferably 100 to 1,000, more preferably 180 to 600. The linking group represented by Q has a molecular weight of preferably 100 to 1,000, more preferably 180 to 600.

The compound having a structure represented by the general formula (A) is more preferably a compound represented by any one of the following general formulas (AA-1) to (AA-3), (AA-6), (AA-7), and (AA-8), a polymer or oligomer having a structure represented by the following general formula (AA-4) in the repeating unit (preferably a polymer or oligomer having a repeating unit of any one of general formulas (AA-4-1) to (AA-4-3)), or a polymer or oligomer having a repeating unit represented by the following general formula (AA-6).

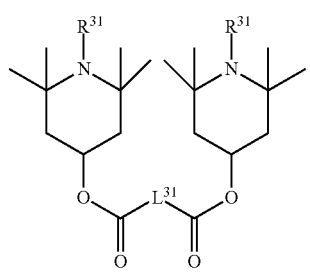

(AA-1)

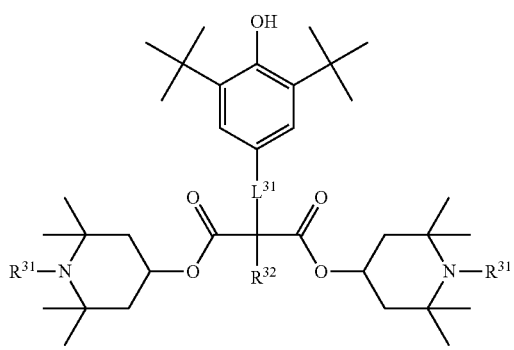

(AA-2)

-continued
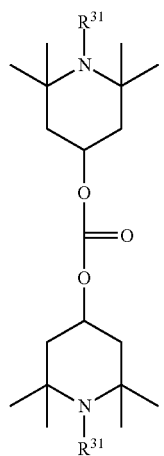
(AA-3)
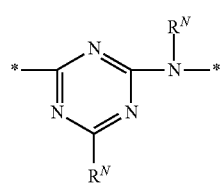
(AA-4)
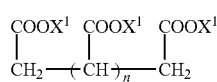
(AA-5)
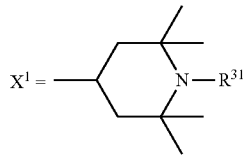
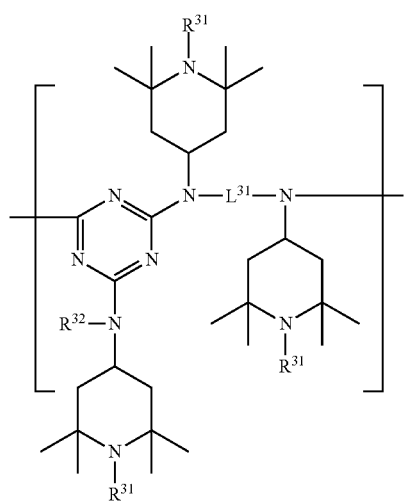
(AA-4-1)
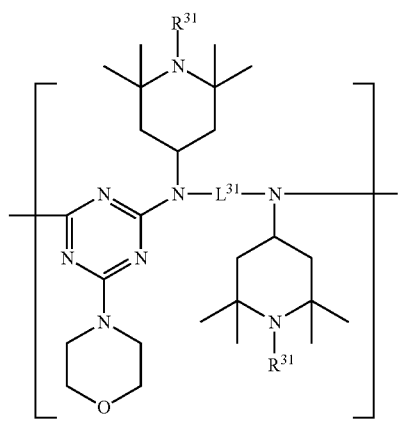
(AA-4-2)
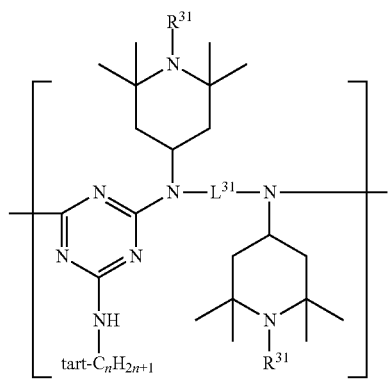
(AA-4-3)
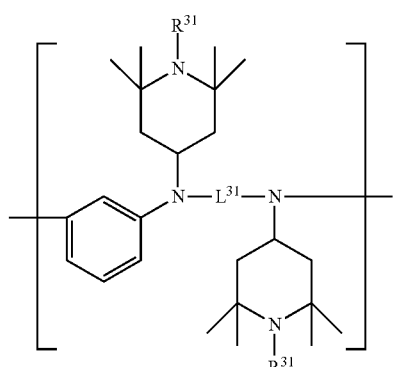
(AA-6)
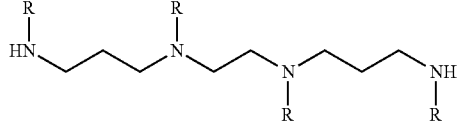
(AA-7)
R = H or
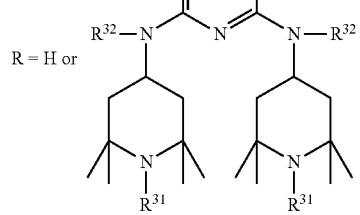

-continued (AA-8)

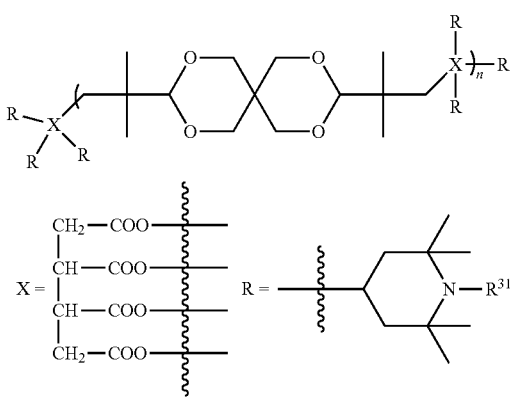

In each of the formulas, $R^{31}$ have the same definition and preferred examples as $R^5$ in the general formula (A).

$R^{32}$ represent a hydrogen atom or an alkyl group having 1 to 20 carbon atoms (preferably 1 to 12 carbon atoms, more preferably 1 to 8 carbon atoms, still more preferably 1 to 6 carbon atoms). $L^{31}$ represents a single bond or an alkylene group having 1 to 20 carbon atoms (preferably 1 to 10 carbon atoms). $R^N$ have the same definition as $R^N$ in the general formula (a-2). n represent an integer of 1 to 20 (preferably 1 to 10) (note that, in the general formula (AA-4-3), n represent an integer of 4 to 20 (preferably 4 to 10)).

In the general formula (AA-4), * represent a bonding site in the compound. In the general formula (AA-7), of R's, at least one is not H and is a group including triazine. In the general formula (AA-8), the wavy lines represent a bonding site.

When the compound having a structure represented by the general formula (A) is a polymer or oligomer, the number of the repeating units (degree of polymerization) is preferably 2 to 100, more preferably 2 to 50, still more preferably 2 to 10. The end structure of the polymer or oligomer is not particularly limited, but may be, for example, a hydrogen atom, a substituted or unsubstituted amino group, or a substituted or unsubstituted triazyl group.

Component (B)

The component (B) is at least one of a compound having a structure represented by a general formula (B-1) below, a compound represented by a general formula (B-2) below, or a compound represented by a general formula (B-3) below.

General formula (B-1)

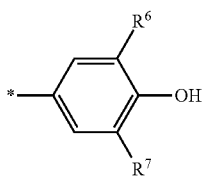

In the general formula (B-1), $R^6$ and $R^7$ are a hydrogen atom, an alkyl group having 1 to 12 carbon atoms (preferably an alkyl group having 1 to 8 carbon atoms such as a methyl group, an ethyl group, an n-butyl group, an isopropyl group, a sec-butyl group, a t-butyl group, a t-pentyl group, a t-hexyl group, or a t-octyl group), or an aralkyl group having 7 to 36 (preferably 7 to 30) carbon atoms. At least one of $R^1$ or $R^2$ is preferably a secondary alkyl group or a tertiary alkyl group; at least one of $R^1$ or $R^2$ is more preferably a tertiary alkyl group. Both of $R^1$ and $R^2$ are also preferably tertiary alkyl groups (preferably t-butyl groups). * represents a bonding site in the compound.

The compound having a structure represented by the general formula (B-1) preferably includes at least one of a compound represented by a general formula (b-1) below or a compound represented by a general formula (b-2) below. In the compound having a structure represented by the general formula (B-1), the total of the contents of the compound represented by the general formula (b-1) below and the compound represented by the general formula (b-2) below is not particularly limited, and is, for example, preferably 50 mass % or more, more preferably 80 mass % or more, still more preferably 90 mass % or more, and may be 100 mass %.

General formula (b-1)

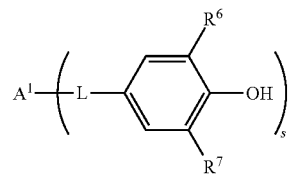

General formula (b-2)

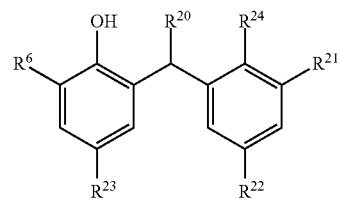

In the general formulas, $R^6$ and $R^7$ respectively have the same definitions as $R^6$ and $R^7$ in the general formula (B-1).

L represents a single bond or a divalent linking group. L is preferably an alkylene group having 1 to 10 carbon atoms (preferably 1 to 5 carbon atoms), an alkenylene group having 2 to 10 carbon atoms (preferably 2 to 5 carbon atoms), or a group represented by $-L^1-C(=O)-O-L^2-$. Here, $L^1$ and $L^2$ represent a single bond, an alkylene group having 1 to 10 carbon atoms (preferably 1 to 5 carbon atoms), a carbonyl group, an oxygen atom, or a combination of the foregoing.

s is an integer of 2 to 4, and $A^1$ represents a di- to tetra-valent linking group. $A^1$ is preferably a di- to tetra-valent organic group; in this organic group, the number of carbon atoms is preferably 1 to 20, more preferably 1 to 15, still more preferably 1 to 12, yet more preferably 1 to 10.

When s is 2 and $A^1$ is a divalent organic group, $A^1$ is preferably a divalent aliphatic group (preferably an alkylene group) having 1 to 10 carbon atoms (preferably 1 to 5 carbon atoms) or an arylene group having 6 to 22 carbon atoms (preferably 6 to 14 carbon atoms).

When s is 3 and $A^1$ is a trivalent linking group, $A^1$ is preferably a group represented by a general formula ($A^1L$) below. In the general formula ($A^1L$) below, * represent linking sites.

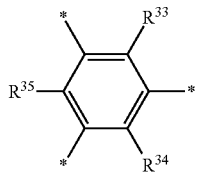

General formula (A¹L)

In the general formula (A¹L), * represent bonding sites. $R^{33}$ to $R^{35}$ represent a hydrogen atom or an alkyl group having 1 to 10 carbon atoms (preferably 1 to 6 carbon atoms, more preferably 1 to 3 carbon atoms).

When s is 4 and A¹ is a tetravalent linking group, A¹ is preferably a quaternary carbon atom. In this case, the linking group L is preferably a group represented by -L¹-C(=O)—O-L²-. Here, L¹ and L² respectively have the same definitions as L¹ and L² above.

$R^{20}$ to $R^{23}$ have the same definitions as $R^6$. $R^{24}$ is a reactive organic substituent, preferably a vinyl-group-containing group, more preferably a (meth)acryloyl-group-containing group.

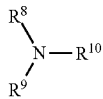

General formula (B-2)

In the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group.

$R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group.

$R^8$ and $R^9$, $R^9$ and $R^{10}$, or $R^8$ and $R^{10}$ may be linked together to form a five- to seven-membered ring without forming a 2,2,6,6-tetraalkylpiperidine skeleton.

In the general formula (B-2), $R^8$ and $R^9$ are not simultaneously hydrogen atoms, and $R^8$ and $R^9$ have 7 or more carbon atoms in total.

In the general formula (B-2), such an aliphatic group (including an aliphatic group constituting a part of a substituent in the general formula (B-2)) means an alkyl group, an alkenyl group, and an alkynyl group. The alkyl group, alkenyl group, and alkynyl group may be linear, branched, or cyclic.

The number of carbon atoms of the alkyl group is preferably 1 to 20, more preferably 1 to 18. Note that, when the alkyl group is branched or cyclic, the lower-limit value of the number of carbon atoms is 3. The same applies to the alkenyl group and the alkynyl group.

The number of carbon atoms of the alkenyl group is preferably 2 to 20, more preferably 2 to 18.

The number of carbon atoms of the alkynyl group is preferably 2 to 20, more preferably 2 to 18. The aliphatic group may have, as a substituent, at least one of the following substituents T.

Substituents T

Halogen Atoms

Fluorine atom, chlorine atom, bromine atom, and iodine atom

Alkyl Groups [Linear, Branched, or Cyclic, Substituted or Unsubstituted Alkyl Groups]

Linear or branched alkyl groups (preferably substituted or unsubstituted alkyl groups having 1 to 30 carbon atoms, such as methyl, ethyl, propyl, isopropyl, t-butyl, octyl, eicosyl, 2-chloroethyl, 2-cyanoethyl, and 2-ethylhexyl)

Cycloalkyl groups (preferably substituted or unsubstituted cycloalkyl groups having 3 to 30 carbon atoms, such as cyclohexyl, cyclopentyl, and 4-dodecylcyclohexyl)

Bicycloalkyl groups (preferably substituted or unsubstituted bicycloalkyl groups having 5 to 30 carbon atoms, in other words, monovalent groups provided by removing a single hydrogen atom from bicycloalkanes having 5 to 30 carbon atoms, such as bicyclo[1.2.2]heptan-2-yl and bicyclo[2.2.2]octan-3-yl)

In the present invention, the cyclic alkyl groups encompass, in addition to the above-described cycloalkyl groups and bicycloalkyl groups (bicyclo-based), polycycloalkyl groups such as tricycloalkyl, tetracycloalkyl, and pentacycloalkyl.

Preferred examples of alkyl groups constituting substituents described below (such as the alkyl groups of alkylthio groups) include the examples of the alkyl groups of Substituents T.

Alkenyl Groups [Linear, Branched, or Cyclic, Substituted or Unsubstituted Alkenyl Groups]

Linear or branched alkenyl groups (preferably substituted or unsubstituted alkenyl groups (number of carbon atoms: 2 to 30), such as vinyl, allyl, prenyl, geranyl, and oleyl)

Cycloalkenyl groups (preferably substituted or unsubstituted cycloalkenyl groups having 3 to 30 carbon atoms, in other words, monovalent groups provided by removing a single hydrogen atom from cycloalkenes having 3 to 30 carbon atoms, such as 2-cyclopenten-1-yl and 2-cyclohexen-1-yl)

Bicycloalkenyl groups (substituted or unsubstituted bicycloalkenyl groups, preferably substituted or unsubstituted bicycloalkenyl groups having 5 to 30 carbon atoms, in other words, monovalent groups provided by removing a single hydrogen atom from bicycloalkenes having a single double bond, which encompass, for example, bicyclo[2.2.1]hept-2-en-1-yl and bicyclo[2.2.2]oct-2-en-4-yl).

Alkynyl Groups [Linear, Branched, or Cyclic, Substituted or Unsubstituted Alkynyl Groups]

Preferably substituted or unsubstituted alkynyl groups having 2 to 30 carbon atoms, such as ethynyl, oropargyl, and trimethylsilylethynyl Aryl Groups Preferably substituted or unsubstituted aryl groups having 6 to 40 carbon atoms (more preferably 6 to 30 carbon atoms, particularly preferably 6 to 20 carbon atoms), such as phenyl, p-tolyl, naphthyl, m-chlorophenyl, and o-hexadecanoylaminophenyl (more preferably phenyl and naphthyl, particularly preferably phenyl); note that, for the substituted aryl groups, aliphatic rings, other aromatic rings, or heterocyclic rings may be fused together.

Heterocyclic Groups

Preferably monovalent groups provided by removing a single hydrogen atom from five- or six-membered, substituted or unsubstituted heterocyclic compounds (including aromatic heterocyclic compounds and non-aromatic heterocyclic compounds), more preferably five- or six-membered, substituted or unsubstituted aromatic heterocyclic groups having 3 to 30 carbon atoms, such as 2-furyl, 2-thienyl, 2-pyrimidinyl, and 2-benzothiazolyl Cyano Group Hydroxy Group Nitro Group Carboxy Group Alkoxy Groups Preferably substituted or unsubstituted alkoxy groups having 1 to 30 carbon atoms, such as methoxy, ethoxy, isopropoxy, t-butoxy, octyloxy, and 2-methoxyethoxy Aryloxy Groups Preferably substituted or unsubstituted aryloxy groups having 6 to 30 carbon atoms, such as phenoxy, 2-methylphenoxy, 4-t-butylphenoxy, 3-nitrophenoxy, 2-tetradecanoylaminophenoxy, and p-methoxyphenoxy Silyloxy Groups Preferably substituted or unsubstituted silyloxy groups having 3 to 20 carbon atoms, such as trim ethyl silyloxy and t-butyl dim ethyl silyloxy Heterocyclic Oxy Groups Preferably substituted or unsubstituted heterocyclic oxy groups having 2 to 30 carbon atoms, such as 1-phenyltetrazole-5-oxy and 2-tetrahydropyranyloxy Acyloxy Groups Preferably a formyloxy group, substituted or unsubstituted alkylcarbonyloxy groups having 2 to 30 carbon atoms, and substituted or unsubstituted aryl carbonyloxy groups having 6 to 30 carbon atoms, such as formyloxy, acetyloxy, pivaloyloxy, stearoyloxy, benzoyloxy, and p-methoxyphenylcarbonyloxy Carbamoyloxy Groups Preferably substituted or unsubstituted carbamoyloxy groups having 1 to 30 carbon atoms, such as N,N-dimethylcarbamoyloxy, N,N-diethylcarbamoyloxy, morpholinocarbonyloxy, N,N-dioctylaminocarbonyloxy, and N-octylcarbamoyloxy Alkoxycarbonyloxy Groups Preferably substituted or unsubstituted alkoxycarbonyloxy groups having 2 to 30 carbon atoms, such as methoxycarbonyloxy, ethoxycarbonyloxy, t-butoxycarbonyloxy, and octyloxycarbonyloxy Aryloxycarbonyloxy Groups Preferably substituted or unsubstituted aryloxycarbonyloxy groups having 7 to 30 carbon atoms, such as phenoxycarbonyloxy, p-methoxyphenoxycarbonyloxy, and p-hexadecyloxyphenoxycarbonyloxy Amino Groups Preferably an amino group, substituted or unsubstituted alkylamino groups having 1 to 30 carbon atoms, and substituted or unsubstituted anilino groups having 6 to 30 carbon atoms (in substituted amino groups and substituted anilino groups, specific examples of the substituents include aliphatic groups, aryl groups, acyl groups, aliphatic sulfonyl groups, and aromatic sulfonyl groups), such as amino, methylamino, dimethylamino, anilino, N-methyl-anilino, and diphenylamino Acylamino Groups Preferably a formylamino group, substituted or unsubstituted alkylcarbonylamino groups having 2 to 30 carbon atoms, and substituted or unsubstituted arylcarbonylamino groups having 6 to 30 carbon atoms, such as formylamino, acetylamino, pivaloylamino, lauroylamino, benzoylamino, and 3,4,5-trioctyloxyphenylcarbonylamino Aminocarbonylamino Groups Preferably substituted or unsubstituted aminocarbonylamino having 1 to 30 carbon atoms, such as carbamoylamino, N,N-dimethylaminocarbonylamino, N,N-diethylaminocarbonylamino, and morpholinocarbonylamino Alkoxycarbonyl Amino Groups Preferably substituted or unsubstituted alkoxycarbonylamino groups having 2 to 30 carbon atoms, such as methoxycarbonylamino, ethoxycarbonylamino, t-butoxycarbonylamino, octadecyloxycarbonylamino, and N-methyl-methoxycarbonylamino Aryloxycarbonylamino Groups Preferably substituted or unsubstituted aryloxycarbonylamino groups having 7 to 30 carbon atoms, such as phenoxycarbonylamino, p-chlorophenoxycarbonylamino, and m-octyloxyphenoxycarbonylamino Sulfamoylamino Groups Preferably substituted or unsubstituted sulfamoylamino groups having 0 to 30 carbon atoms, such as sulfamoylamino, N,N-dimethylaminosulfonylamino, and N-octyl aminosulfonylamino Alkyl or Aryl Sulfonylamino Groups Preferably substituted or unsubstituted alkyl sulfonylamino groups having 1 to 30 carbon atoms and substituted or unsubstituted aryl sulfonylamino groups having 6 to 30 carbon atoms, such as methylsulfonylamino, butylsulfonylamino, phenylsulfonylamino, 2,3,5-trichlorophenylsulfonylamino, and p-methylphenyl sulfonylamino Sulfanyl Group Alkylthio Groups Preferably substituted or unsubstituted alkylthio groups having 1 to 30 carbon atoms, such as methylthio, ethylthio, hexadecylthio, and octylthio Arylthio Groups Preferably substituted or unsubstituted arylthio having 6 to 30 carbon atoms, such as phenylthio, p-chlorophenylthio, m-methoxyphenylthio, and p-methoxyphenylthio Heterocyclic Thio Groups Preferably substituted or unsubstituted heterocyclic thio groups having 2 to 30 carbon atoms, such as 2-benzothiazolylthio and 1-phenyltetrazol-5-ylthio Sulfamoyl Groups Preferably substituted or unsubstituted sulfamoyl groups having 0 to 30 carbon atoms, such as N-ethyl sulfamoyl, N-(3-dodecyloxypropyl)sulfamoyl, N,N-dimethylsulfamoyl, N-acetylsulfamoyl, N-benzoylsulfamoyl, and N—(N'-phenylcarbamoyl)sulfamoyl Sulfo Group Alkyl or Aryl Sulfinyl Groups Preferably substituted or unsubstituted alkyl sulfinyl groups having 1 to 30 carbon atoms and substituted or unsubstituted aryl sulfinyl groups having 6 to 30 carbon atoms, such as methylsulfinyl, ethylsulfinyl, phenylsulfinyl, and p-methylphenylsulfinyl Alkyl or Aryl Sulfonyl Groups Preferably substituted or unsubstituted alkylsulfonyl groups having 1 to 30 carbon atoms and substituted or unsubstituted aryl sulfonyl groups having 6 to 30 carbon atoms, such as methyl sulfonyl, ethyl sulfonyl, butyl sulfonyl, phenyl sulfonyl, and p-methylphenylsulfonyl Acyl Groups Preferably a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms (in the heterocyclic carbonyl groups, carbon atoms in the heterocyclic rings are bonded to the carbon atoms of the carbonyl groups), such as acetyl, pivaloyl, 2-chloroacetyl, stearoyl, benzoyl, p-octyloxyphenylcarbonyl, 2-pyridylcarbonyl, 2-furylcarbonyl, and (meth)acryloyl Aryloxycarbonyl Groups Preferably substituted or unsubstituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl Alkoxycarbonyl Groups Preferably substituted or unsubstituted alkoxycarbonyl groups having 2 to 30 carbon atoms, such as methoxycarbonyl, ethoxycarbonyl, t-butoxycarbonyl, hexadecyloxycarbonyl, and octadecyloxycarbonyl Carbamoyl Groups Preferably substituted or unsubstituted carbamoyl groups having 1 to 30 carbon atoms, such as carbamoyl, N-methylcarbamoyl, N,N-dimethylcarbamoyl, N,N-dioctylcarbamoyl, and N-(methylsulfonyl)carbamoyl Aryl or Heterocyclic Azo Groups Preferably substituted or unsubstituted aryl azo groups having 6 to 30 carbon atoms and substituted or unsubstituted heterocyclic azo groups having 3 to 30 carbon atoms, such as phenylazo, p-chlorophenylazo, and 5-ethylthio-1,3,4-thiadiazol-2-ylazo Imide Groups Preferably N-succinimide and N-phthalimide Phosphino Groups Preferably substituted or unsubstituted phosphino groups having 2 to 30 carbon atoms, such as dimethylphosphino, diphenylphosphino, and methylphenoxyphosphino Phosphinyl Groups Preferably a phosphinyl group and substituted or unsubstituted phosphinyl groups having 2 to 30 carbon atoms, such as phosphinyl, dioctyloxyphosphinyl, and diethoxyphosphinyl Phosphinyloxy Groups Preferably substituted or unsubstituted phosphinyloxy groups having 2 to 30 carbon atoms, such as diphenoxyphosphinyloxy and dioctyloxyphosphinyloxy Phosphinylamino Groups Preferably substituted or unsubstituted phosphinylamino groups having 2 to 30 carbon atoms, such as dimethoxyphosphinylamino and dimethylaminophosphinylamino Silyl Groups Preferably substituted or unsubstituted silyl groups having 3 to 30 carbon atoms, such as trim ethyl silyl, t-butyl dim ethyl silyl, and phenyl dim ethyl silyl Of the above-described substituents T, for those having a hydrogen atom, such hydrogen atoms may be further substituted with the above-described groups. Examples of such a substituent include alkyl carbonylaminosulfonyl groups, aryl carbonylaminosulfonyl groups, alkyl sulfonylaminocarbonyl groups, and aryl sulfonylaminocarbonyl groups. Examples include methylsulfonylaminocarbonyl, p-methylphenylsulfonylaminocarbonyl, acetylaminosulfonyl, and benzoylaminosulfonyl groups.

Specific examples of the acyl group in the general formula (B-2) include the acyl groups of the substituents T.

Specific examples of the aliphatic oxycarbonyl group in the general formula (B-2) include the alkoxycarbonyl groups of the substituents T.

Specific examples of the aromatic oxycarbonyl group in the general formula (B-2) include the aryloxycarbonyl groups of the substituents T.

Specific examples of the aliphatic sulfonyl group in the general formula (B-2) include the alkylsulfonyl groups of the substituents T.

Specific examples of the aromatic sulfonyl group in the general formula (B-2) include the aryl sulfonyl groups of the substituents T.

Specific examples of the aliphatic oxy group in the general formula (B-2) include the alkoxy groups of the substituents T.

Specific examples of the aromatic oxy group in the general formula (B-2) include the aryloxy groups of the substituents T.

Specific examples of the aliphatic thio group in the general formula (B-2) include the alkylthio groups of the substituents T.

Specific examples of the aromatic thio group in the general formula (B-2) include the arylthio groups of the substituents T.

Specific examples of the acyloxy group in the general formula (B-2) include the acyloxy groups of the substituents T.

Specific examples of the aliphatic oxycarbonyloxy group in the general formula (B-2) include the alkoxycarbonyloxy groups of the substituents T.

Specific examples of the aromatic oxycarbonyloxy group in the general formula (B-2) include the aryloxycarbonyloxy groups of the substituents T.

Specific examples of the substituted amino group in the general formula (B-2) include the substituted amino groups of the substituents T.

In the general formula (B-2), the heterocyclic group preferably includes a five-membered or six-membered, saturated or unsaturated heterocyclic ring. To the heterocyclic ring, an aliphatic ring, an aromatic ring, or another heterocyclic ring may be fused. Examples of the heteroatom of the heterocyclic ring include B, N, O, S, Se, and Te. Such heteroatoms are preferably N, O, and S. In the heterocyclic ring, a carbon atom preferably has a free valance (monovalent) (the heterocyclic group is bonded via the carbon atom). The number of carbon atoms of the heterocyclic group is preferably 1 to 40, more preferably 1 to 30, still more preferably 1 to 20. Examples of the saturated heterocyclic ring include a pyrazolidine ring, a pyrrolidine ring, a morpholine ring, a 2-bora-1,3-dioxolane ring, and a 1,3-thiazolidine ring (note that the piperidine ring is excluded). Examples of the unsaturated heterocyclic ring include an imidazole ring, a thiazole ring, a benzothiazole ring, a benzooxazole ring, a benzotriazole ring, a benzoselenazole ring, a pyridine ring, a pyrimidine ring, and a quinoline ring. The heterocyclic group may have a substituent. Examples of the substituent include the above-described substituents T.

In the general formula (B-2), $R^8$ and $R^9$ have a total number of carbon atoms of 7 or more, preferably 7 to 70, more preferably 7 to 40.

The compound represented by the general formula (B-2) and used in the present invention encompasses the compounds represented by, for example, the general formula (I) in JP1994-97332B (JP-H6-97332B), the general formula (I) in JP1994-97334B (JP-H6-97334B), the general formula (I) in JP1990-148037A (JP-H2-148037A), the general formula (I) in JP1990-150841A (JP-H2-150841A), the general formula (I) in JP1990-181145A (JP-H2-181145A), the general formula (I) in JP1991-266836A (JP-H3-266836A), the general formula (IV) in JP1992-350854A (JP-H4-350854A), and the general formula (I) in JP1993-61166A (JP-H5-61166A).

The compound represented by the general formula (B-2) is preferably a compound represented by the following general formula (B-2a) or (B-2b).

General formula (B-2a)

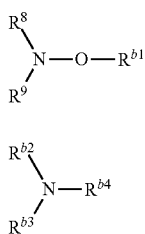

General formula (B-2b)

$R^{b2}$
 \
  N—$R^{b4}$
 /
$R^{b3}$

In the general formula (B-2a), $R^8$ and $R^9$ respectively have the same definitions as $R^8$ and $R^9$ in the general formula (B-2). $R^{b1}$ has the same definition as $R^8$.

In the general formula (B-2b), $R^{b2}$ to $R^{b4}$ represent an aliphatic group or an acyl group. As the aliphatic group and the acyl group, the aliphatic group and the acyl group that can be represented by $R^8$ in the general formula (B-2) can be respectively employed.

The following are specific examples of the compound represented by the general formula (B-2); however, the present invention is not limited to these.

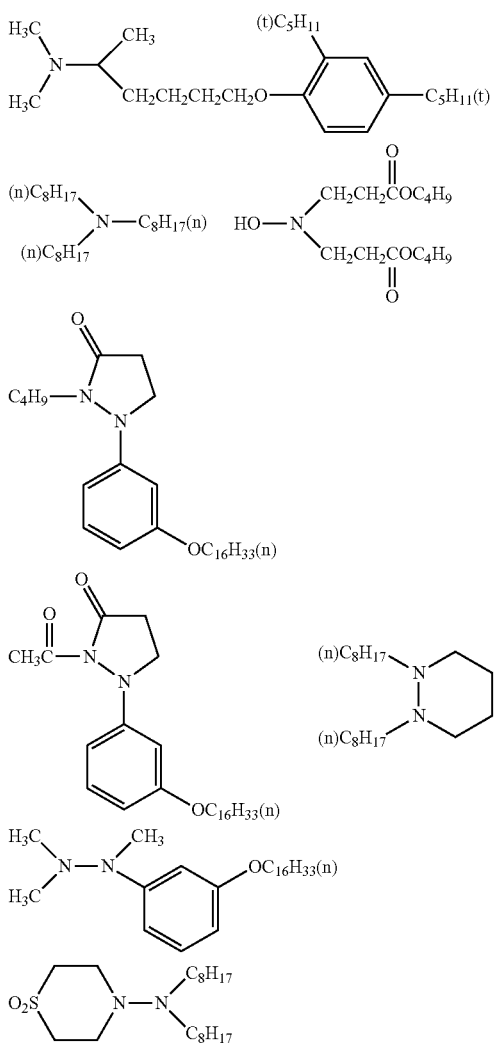

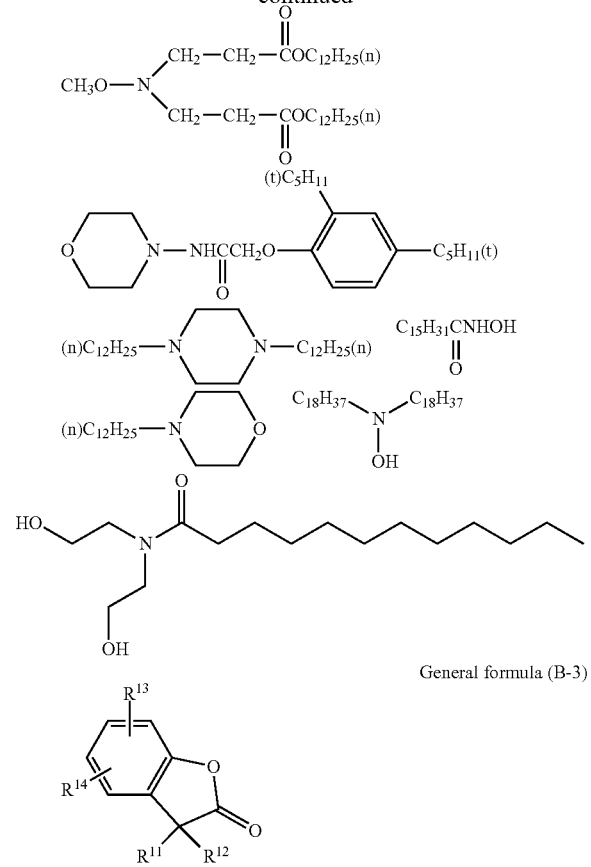

General formula (B-3)

In the general formula (B-3), $R^{11}$ to $R^{14}$ represent a hydrogen atom, an alkyl group having 1 to 20 carbon atoms, an aralkyl group having 7 to 20 carbon atoms, or an aryl group having 6 to 15 carbon atoms. The substituents represented by $R^{11}$ to $R^{14}$ may have at least one of the above-described substituents T.

In the general formula (B-3), the alkyl group having 1 to 20 carbon atoms may be a linear or branched alkyl group. Examples include methyl, ethyl, propyl, isopropyl, butyl, isobutyl, pentyl, 2-ethylbutyl, hexyl, heptyl, octyl, 2-ethylhexyl, nonyl, decyl, dodecyl, tetradecyl, octadecyl, eicosyl, benzyl, 2,6-di-t-butyl-4-methylbenzyl, phenethyl, phenylpropyl, naphthylmethyl, and 2-phenylisopropyl. When the alkyl group has a substituent, the above-described number of carbon atoms includes the number of the carbon atoms of the substituent.

In the general formula (B-3), examples of the aryl group having 6 to 15 carbon atoms include phenyl, tolyl, and naphthyl. When the aryl group has a substituent, for the above-described number of carbon atoms, the substituent is included.

In the general formula (B-3), $R^{11}$ and $R^{12}$ are preferably a combination of a hydrogen atom and an aryl group having 7 to 20 carbon atoms. In particular, preferred is a combination of a hydrogen atom and an aryl group having 8 to 20 carbon atoms, more preferred is a combination of a hydrogen atom and an aryl group having 8 to 18 carbon atoms, and particularly preferred is a combination of a hydrogen atom and 3,4-dimethylphenyl.

In the general formula (B-3), $R^{13}$ and $R^{14}$ are, of these, preferably an alkyl group having 1 to 20 carbon atoms, more preferably an alkyl group having 2 to 20 carbon atoms, still more preferably an alkyl group having 3 to 20 carbon atoms, particularly preferably t-butyl.
Specific examples of the compound represented by the general formula (B-3) include the following compounds. However, the present invention is not limited to these.
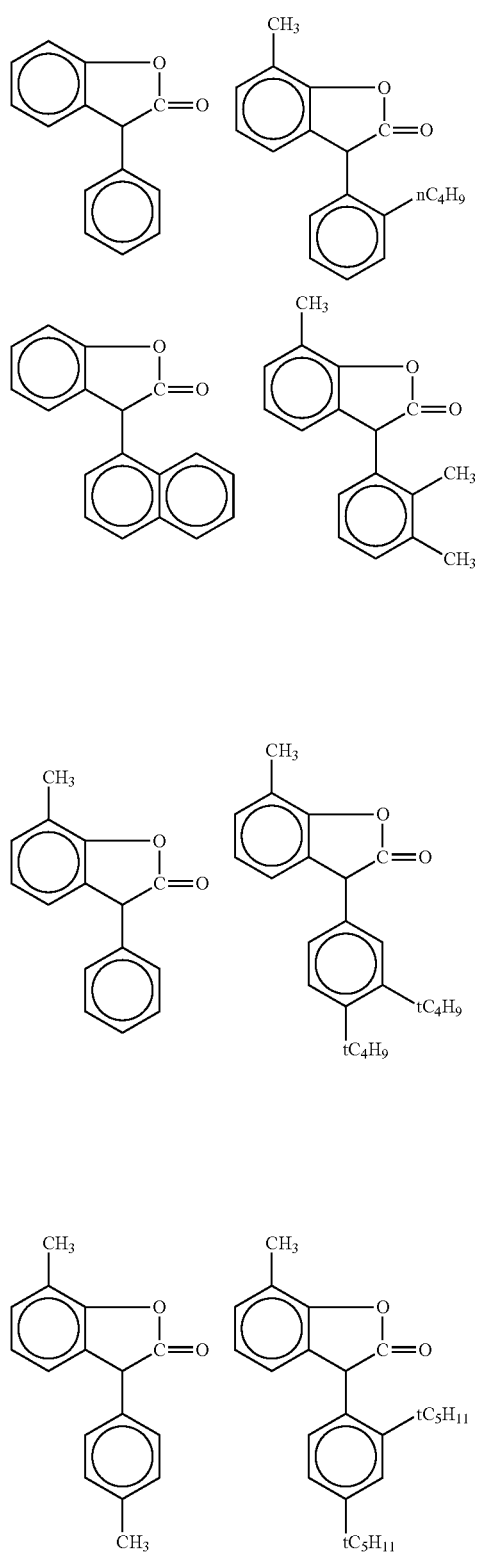
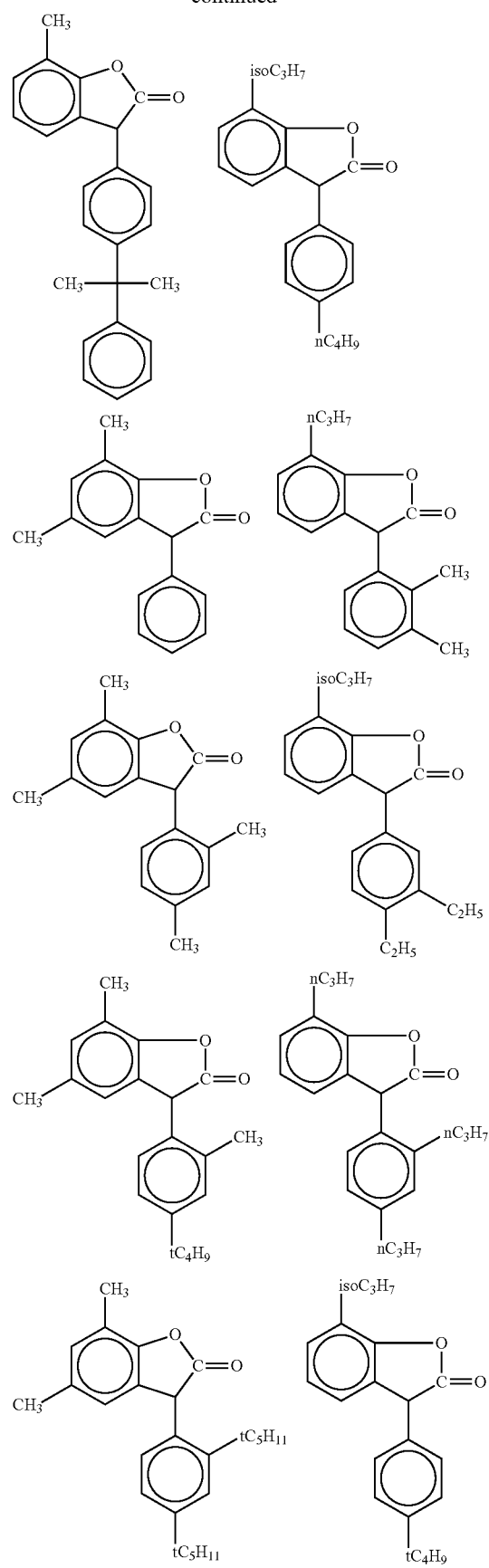

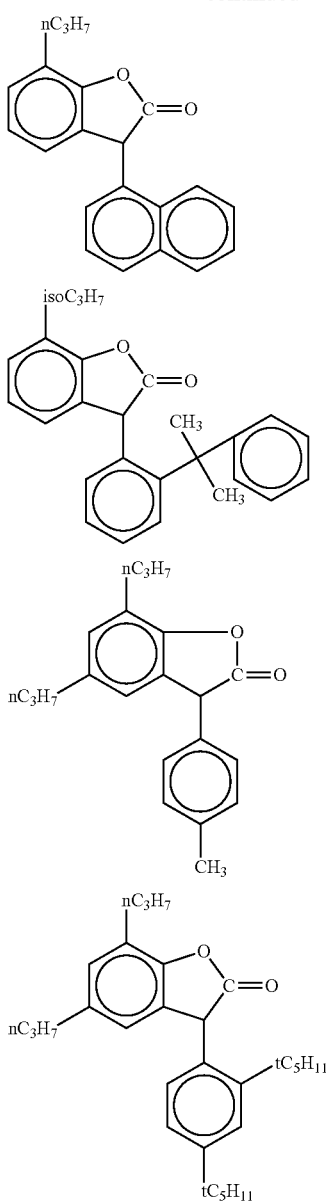
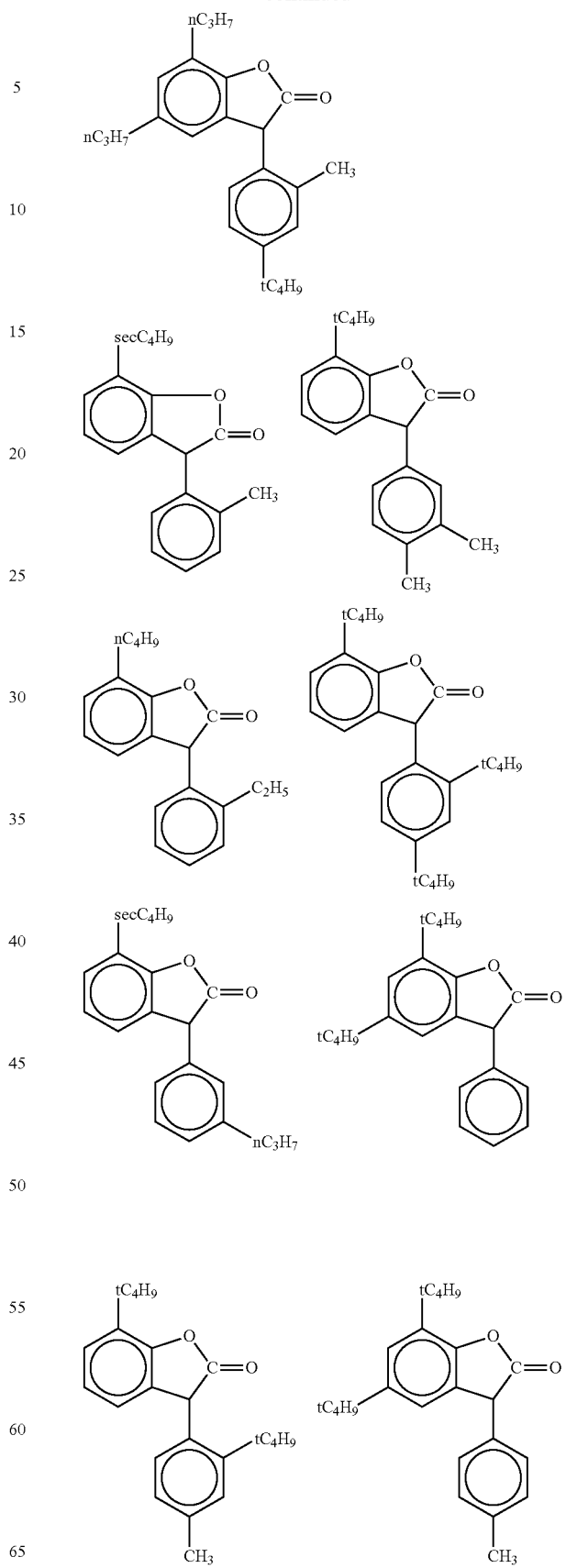

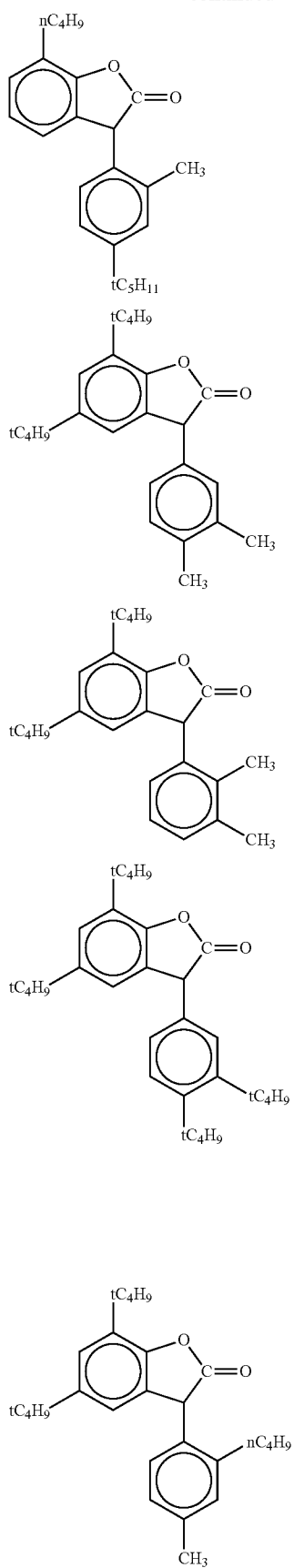
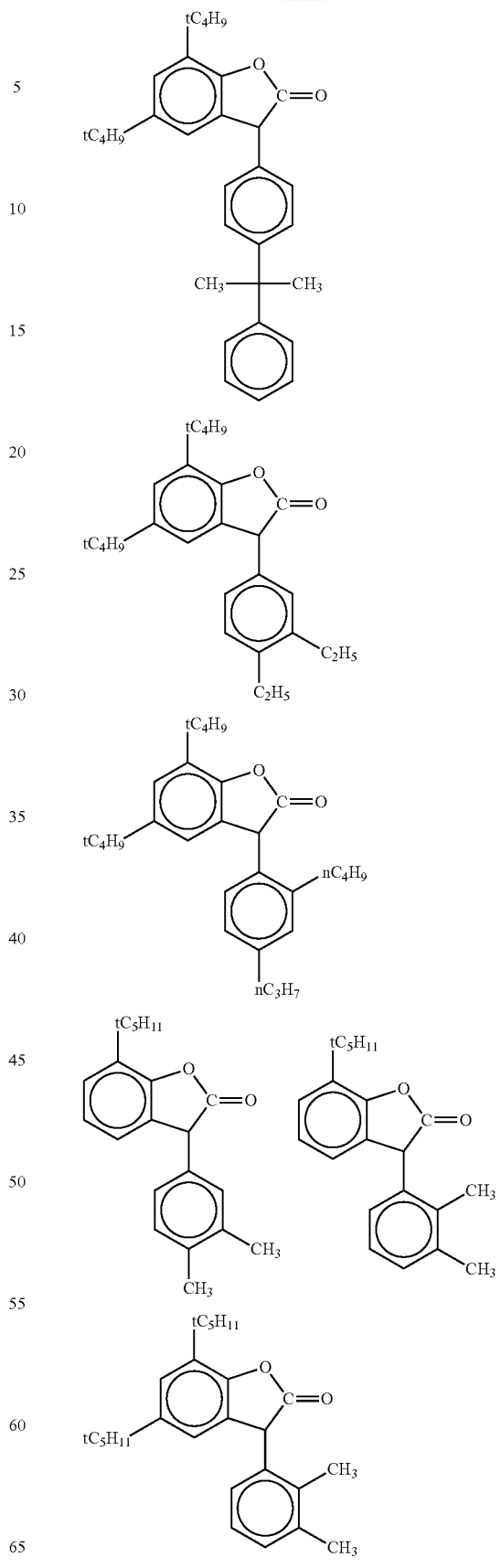

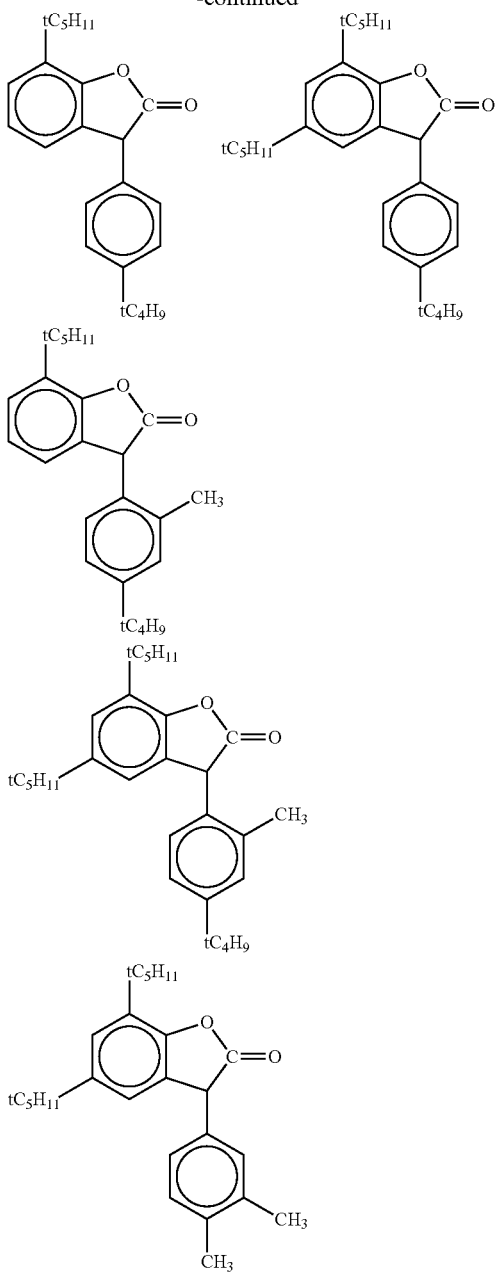

Component (C)

The component (C) is at least one of a compound represented by a formula (C-1) below, a compound having a structure represented by a general formula (C-2) below, or a compound having a structure represented by a general formula (C-3) below.

Formula (C-1)

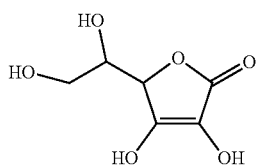

General formula (C-2)

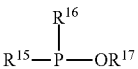

In the general formula (C-2), $R^{15}$ and $R^{16}$ represent an alkyl group, an aryl group, an alkoxy group, an aryloxy group, or a halogen atom, and $R^{17}$ represents an alkyl group or an aryl group. At least two of $R^{15}$, $R^{16}$, and $R^{17}$ may be linked together via a di- or higher valent group or a single bond.

In the present invention, the compound having a structure represented by the general formula (C-2) includes, in addition to the compound represented by the general formula (C-2), the following compounds (a) and (b).

(a) a compound having a structure in which a monovalent group provided by removing a single hydrogen atom from $R^{15}$, $R^{16}$, or $R^{17}$ is linked to, via a di- or higher valent group or a single bond, at least one of $R^{15}$, $R^{16}$, or $R^{17}$ of other one or more (preferably an integer of 1 to 3) compounds represented by the general formula (C-2) and, (b) a compound having a structure in which a di- or higher valent group provided by removing, in total, two or more hydrogen atoms from at least one group selected from the group consisting of $R^{15}$, $R^{16}$, and $R^{17}$ (for example, in the case of removing two hydrogen atoms, a divalent group is provided; in the case of removing three hydrogen atoms, a trivalent group is provided) is linked to, via a di- or higher valent group or a single bond, at least one of $R^{15}$, $R^{16}$, or $R^{17}$ of other one or more (preferably an integer of 1 to 3) compounds represented by the general formula (C-2).

In other words, in the present invention, the compound having a structure represented by the general formula (C-2) is defined to include the compound represented by the general formula (C-2) and the compounds having a structure in which, in a single molecule, a plurality of structures represented by the general formula (C-2) are present.

In the general formula (C-2), the alkyl groups represented by $R^{15}$, $R^{16}$, and $R^{17}$ represent linear, branched, or cyclic, substituted or unsubstituted alkyl groups preferably having 1 to 50 carbon atoms, more preferably having 1 to 30 carbon atoms, particularly preferably having 1 to 20 carbon atoms. Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred include methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl; still more preferred include methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

The alkyl groups represented by $R^{15}$, $R^{16}$, and $R^{17}$ may further have a substituent. Examples of the substituent include halogen atoms, alkyl groups (including cycloalkyl groups), alkenyl groups (including cycloalkenyl groups and bicycloalkenyl groups), alkynyl groups, aryl groups, a cyano group, a hydroxy group, a nitro group, a carboxy group, alkoxy groups, aryloxy groups, acyloxy groups, a carbamoyloxy group, alkoxycarbonyloxy groups, aryloxycarbonyloxy groups, amino groups (including an anilino group), acylamino groups, an aminocarbonylamino group, alkoxycarbonylamino groups, aryloxycarbonylamino groups, acyl groups, aryloxycarbonyl groups, alkoxycarbonyl groups, and a carbamoyl group.

More specifically, examples of the substituent include halogen atoms (such as a chlorine atom, a bromine atom, and an iodine atom), alkyl groups [(which represent linear, branched, or cyclic, substituted or unsubstituted alkyl groups. These encompass, for example, alkyl groups (preferably alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl), cycloalkyl groups (preferably substituted or unsubstituted cycloalkyl groups having 3 to 30 carbon atoms, such as cyclohexyl, cyclopentyl, and 4-n-dodecylcyclohexyl), bicycloalkyl groups (preferably substituted or unsubstituted bicycloalkyl groups having 5 to 30 carbon atoms, in other words, monovalent groups provided by removing a single hydrogen atom from bicycloalkanes having 5 to 30 carbon atoms, such as bicyclo[1.2.2]heptan-2-yl and bicyclo[2.2.2]octan-3-yl), and tricyclo structures having more cyclic structures. Alkyl groups in substituents described below (such as alkyl groups of alkylthio groups) also represent alkyl groups having such concepts), alkenyl groups (preferably substituted or unsubstituted alkenyl groups having 2 to 30 carbon atoms, such as vinyl, allyl, prenyl, geranyl, and oleyl), cycloalkenyl groups (preferably substituted or unsubstituted cycloalkenyl groups having 3 to 30 carbon atoms, in other words, monovalent groups provided by removing a single hydrogen atom from cycloalkenes having 3 to 30 carbon atoms, such as 2-cyclopenten-1-yl and 2-cyclohexen-1-yl), bicycloalkenyl groups (substituted or unsubstituted bicycloalkenyl groups, preferably, substituted or unsubstituted bicycloalkenyl groups having 5 to 30 carbon atoms, in other words, monovalent groups provided by removing a single hydrogen atom from bicycloalkenes having a single double bond, such as bicyclo [2.2.1]hept-2-en-1-yl and bicyclo[2.2.2]oct-2-en-4-yl) are encompassed], alkynyl groups (preferably substituted or unsubstituted alkynyl groups having 2 to 30 carbon atoms, such as ethynyl, propargyl, and trimethylsilylethynyl), aryl groups (preferably substituted or unsubstituted aryl groups having 6 to 30 carbon atoms, such as phenyl, p-tolyl, naphthyl, m-chlorophenyl, and o-hexadecanoylaminophenyl), heterocyclic groups (preferably monovalent groups provided by removing a single hydrogen atom from five- or six-membered, substituted or unsubstituted, aromatic or non-aromatic heterocyclic compounds, more preferably five-membered or six-membered, aromatic heterocyclic groups having 3 to 30 carbon atoms, such as 2-furanyl, 2-thienyl, 2-pyrimidinyl, and 2-benzothiazolinyl), a cyano group, a hydroxy group, a nitro group, a carboxy group, alkoxy groups (preferably substituted or unsubstituted alkoxy groups having 1 to 32 carbon atoms, such as methoxy, ethoxy, isopropoxy, t-butoxy, n-octyloxy, and 2-methoxyethoxy, aryloxy groups (preferably substituted or unsubstituted aryloxy groups having 6 to 30 carbon atoms, such as phenoxy, 2-methylphenoxy, 4-t-butylphenoxy, 3-nitrophenoxy, and 2-tetradecanoylaminophenoxy), silyloxy groups (preferably silyloxy groups having 3 to 20 carbon atoms, such as trimethylsilyloxy and t-butyldimethylsilyloxy), heterocyclic oxy groups (preferably substituted or unsubstituted heterocyclic oxy groups having 2 to 30 carbon atoms, 1-phenyltetrazole-5-oxy, and 2-tetrahydropyranyloxy), acyloxy groups (preferably a formyloxy group, substituted or unsubstituted alkylcarbonyloxy groups having 2 to 30 carbon atoms, substituted or unsubstituted arylcarbonyloxy groups having 6 to 30 carbon atoms, such as formyloxy, acetyloxy, pivaloyloxy, stearoyloxy, benzoyloxy, and p-methoxyphenylcarbonyloxy), carbamoyloxy groups (preferably substituted or unsubstituted carbamoyloxy groups having 1 to 30 carbon atoms, such as N,N-dimethylcarbamoyloxy, N,N-diethylcarbamoyloxy, morpholinocarbonyloxy, N,N-di-n-octylaminocarbonyloxy, and N-n-octylcarbamoyloxy), alkoxycarbonyloxy groups (preferably substituted or unsubstituted alkoxycarbonyloxy groups having 2 to 30 carbon atoms, such as methoxycarbonyloxy, ethoxycarbonyloxy, t-butoxycarbonyloxy, and n-octylcarbonyloxy, aryloxycarbonyloxy groups (preferably substituted or unsubstituted aryloxycarbonyloxy groups having 7 to 30 carbon atoms, such as phenoxycarbonyloxy, p-methoxyphenoxycarbonyloxy, and p-n-hexadecyloxyphenoxycarbonyloxy), amino groups (preferably an amino group, substituted or unsubstituted alkylamino groups having 1 to 30 carbon atoms, and substituted or unsubstituted anilino groups having 6 to 30 carbon atoms, such as amino, methylamino, dimethylamino, anilino, N-methyl-anilino, and diphenylamino), acylamino groups (preferably a formylamino group, substituted or unsubstituted alkylcarbonylamino groups having 1 to 30 carbon atoms, and substituted or unsubstituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino), aminocarbonyl amino groups (preferably substituted or unsubstituted aminocarbonylamino having 1 to 30 carbon atoms, such as carbamoylamino, N,N-dimethylaminocarbonylamino, N,N-diethylaminocarbonylamino, and morpholinocarbonylamino), alkoxycarbonylamino groups (preferably substituted or unsubstituted alkoxycarbonylamino groups having 2 to 30 carbon atoms, such as methoxycarbonylamino, ethoxycarbonylamino, t-butoxycarbonylamino, n-octadecyloxycarbonylamino, and N-methyl-methoxycarbonylamino), aryloxycarbonylamino groups (preferably substituted or unsubstituted aryloxycarbonylamino groups having 7 to 30 carbon atoms, such as phenoxycarbonylamino, p-chlorophenoxycarbonylamino, and m-n-octyloxyphenoxycarbonylamino), sulfamoylamino groups (preferably substituted or unsubstituted sulfamoylamino groups having 0 to 30 carbon atoms, such as sulfamoylamino, N,N-dimethylaminosulfonylamino, and N-n-octylaminosulfonylamino), alkyl and aryl sulfonylamino groups (preferably substituted or unsubstituted alkylsulfonylamino having 1 to 30 carbon atoms, and substituted or unsubstituted aryl sulfonylamino having 6 to 30 carbon atoms, such as methyl sulfonyl amino, butyl sulfonylamino, phenyl sulfonyl amino, 2,3,5-trichlorophenylsulfonylamino, and p-methylphenylsulfonylamino), a sulfanyl group, alkylthio groups (preferably substituted or unsubstituted alkylthio groups having 1 to 30 carbon atoms, such as methylthio, ethylthio, and n-hexadecylthio), arylthio groups (preferably substituted or unsubstituted arylthio having 6 to 30 carbon atoms, such as phenylthio, p-chlorophenylthio, and m-methoxyphenylthio), heterocyclic thio groups (preferably substituted or unsubstituted heterocyclic thio groups having 2 to 30 carbon atoms, such as 2-benzothiazolylthio and 1-phenyltetrazol-5-ylthio), sulfamoyl groups (preferably substituted or unsubstituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, N—(N'-phenylcarbamoyl)sulfamoyl), a sulfo group, alkyl and aryl sulfinyl groups (preferably substituted or unsubstituted alkylsulfinyl groups having 1 to 30 carbon atoms, and substituted or unsubstituted aryl sulfinyl groups having 6 to 30 carbon atoms, such as methylsulfinyl, ethylsulfinyl, phenylsulfinyl, and p-methylphenylsulfinyl), alkyl and aryl sulfonyl groups (preferably substituted or unsubstituted alkyl sulfonyl groups having 1 to 30 carbon atoms, and substituted or unsubstituted aryl sulfonyl groups having 6 to 30 carbon atoms, such as methylsulfonyl, ethylsulfonyl, phenylsulfonyl, and p-methylphenylsulfonyl), acyl groups (preferably a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms and bonded to, via a carbon atom, the carbonyl group, such as acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably substituted or unsubstituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl), alkoxycarbonyl groups (preferably substituted or unsubstituted alkoxycarbonyl groups having 2 to 30 carbon atoms, such as methoxycarbonyl, ethoxycarbonyl, t-butoxycarbonyl, and n-octadecyloxycarbonyl), carbamoyl groups (preferably substituted or unsubstituted carbamoyl having 1 to 30 carbon atoms, such as carbamoyl, N-methylcarbamoyl, N,N-dimethylcarbamoyl, N,N-di-n-octylcarbamoyl, and N-(methylsulfonyl)carbamoyl), aryl and heterocyclic azo groups (preferably substituted or unsubstituted aryl azo groups having 6 to 30 carbon atoms, and substituted or unsubstituted heterocyclic azo groups having 3 to 30 carbon atoms, such as phenylazo, p-chlorophenylazo, and 5-ethylthio-1,3,4-thiadiazol-2-ylazo), imide groups (preferably N-succinimide and N-phthalimide), phosphino groups (preferably substituted or unsubstituted phosphino groups having 2 to 30 carbon atoms, such as dimethylphosphino, diphenylphosphino, and methylphenoxyphosphino), phosphinyl groups (preferably substituted or unsubstituted phosphinyl groups having 2 to 30 carbon atoms, such as phosphinyl, dioctyloxyphosphinyl, and diethoxyphosphinyl), phosphinyloxy groups (preferably substituted or unsubstituted phosphinyloxy groups having 2 to 30 carbon atoms, such as diphenoxyphosphinyloxy, and dioctyloxyphosphinyloxy), phosphinylamino groups (preferably substituted or unsubstituted phosphinylamino groups having 2 to 30 carbon atoms, such as dimethoxyphosphinylamino and dimethylaminophosphinylamino), and silyl groups (preferably substituted or unsubstituted silyl groups having 3 to 30 carbon atoms, such as trim ethyl silyl, t-butyl dim ethyl silyl, and phenyl dim ethyl silyl).

Of the above-described substituents, for those having a hydrogen atom, such hydrogen atoms may be further substituted with the above-described substituents. Examples of such substituents include alkylcarbonylaminosulfonyl groups, arylcarbonylaminosulfonyl groups, alkyl sulfonylaminocarbonyl groups, aryl sulfonylaminocarbonyl groups, a methyl sulfonylaminocarbonyl group, a p-methylphenylsulfonylaminocarbonyl group, an acetylaminosulfonyl group, and a benzoylaminosulfonyl group.

The aryl groups represented by $R^{15}$, $R^{16}$ and $R^{17}$ represent substituted or unsubstituted aryl groups preferably having 6 to 50 carbon atoms, more preferably 6 to 30 carbon atoms, particularly preferably 6 to 20 carbon atoms. Preferred examples include phenyl, 2-methylphenyl, 3-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 3-chlorophenyl, 4-chlorophenyl, 2-methoxyphenyl, 3-methoxyphenyl, 4-methoxyphenyl, 2-benzylphenyl, 4-benzylphenyl, 2-methylcarbonylphenyl, and 4-methylcarbonylphenyl.

The aryl groups represented by $R^{15}$, $R^{16}$, and $R^{17}$ are more preferably phenyl, 2-methylphenyl, 4-methylphenyl, 2-ethylphenyl, 4-ethylphenyl, 2,4-dimethylphenyl, 2,6-dimethylphenyl, 2,4,6-trimethylphenyl, 1-naphthyl, 2-naphthyl, 2-chlorophenyl, 4-chlorophenyl, 2-methoxyphenyl, 3-methoxyphenyl, 4-methoxyphenyl, 2-benzylphenyl, or 4-benzylphenyl, particularly preferably phenyl.

The above-described aryl groups represented by $R^{15}$, $R^{16}$, and $R^{17}$ may further have a substituent. Examples of the substituent include the above-described substituents that the alkyl groups represented by $R^{15}$, $R^{16}$, and $R^{17}$ may have.

The alkoxy groups represented by $R^{15}$ and $R^{16}$ represent linear, branched, or cyclic, substituted or unsubstituted alkoxy groups. They preferably have 1 to 50 carbon atoms, more preferably 1 to 30 carbon atoms, particularly preferably 1 to 20 carbon atoms. Preferred examples include methoxy, ethoxy, n-propoxy, isopropoxy, cyclopropoxy, butoxy, isobutoxy, t-butoxy, s-butoxy, pentyloxy, isopentyloxy, neopentyloxy, t-pentyloxy, hexyloxy, cyclohexyloxy, heptyloxy, cyclopentyloxy, octyloxy, 2-ethylhexyloxy, nonyloxy, decyloxy, dodecyloxy, tetradecyloxy, hexadecyloxy, octadecyloxy, eicosyloxy, docosyloxy, and triacontyloxy. More preferred include methoxy, ethoxy, n-propoxy, isopropoxy, butoxy, isobutoxy, t-butoxy, s-butoxy, pentyloxy, isopentyloxy, neopentyloxy, hexyloxy, cyclohexyloxy, octyloxy, 2-ethylhexyloxy, dodecyloxy, hexadecyloxy, and octadecyloxy, particularly preferred include methoxy, ethoxy, n-propoxy, isopropoxy, t-butoxy, pentyloxy, isopentyloxy, hexyloxy, cyclohexyloxy, octyloxy, 2-ethylhexyloxy, dodecyloxy, hexadecyloxy, and octadecyloxy.

The above-described alkoxy groups represented by $R^{15}$ and $R^{16}$ may further have a substituent. Examples of the substituent include the above-described substituents that the alkyl groups represented by $R^{15}$, $R^{16}$, and $R^{17}$ may have.

The aryloxy groups represented by $R^{15}$ and $R^{16}$ represent substituted or unsubstituted aryloxy groups having preferably 6 to 50 carbon atoms, more preferably 6 to 30 carbon atoms, particularly preferably 6 to 20 carbon atoms. Preferred examples include phenoxy, 2-methylphenoxy, 3-methylphenoxy, 4-methylphenoxy, 2-ethylphenoxy, 4-ethylphenoxy, 2,4-dimethylphenoxy, 2,4-di-t-butylphenoxy, 2,6-di-t-butylphenoxy, 2,6-dimethylphenoxy, 2,6-di-t-butyl-4-methylphenoxy, 2,4,6-trimethylphenoxy, 2,4,6-tri-t-butylphenoxy, 1-naphthyloxy, 2-naphthyloxy, 2-chlorophenoxy, 3-chlorophenoxy, 4-chlorophenoxy, 2-methoxyphenoxy, 3-methoxyphenoxy, 4-methoxyphenoxy, 2-benzylphenoxy, 4-benzylphenoxy, 2-methylcarbonylphenoxy, and 4-methylcarbonylphenoxy.

More preferred examples include phenyl, 2,4-di-t-butylphenoxy, and 2,4,6-tri-t-butylphenoxy.

The above-described aryloxy groups represented by $R^{15}$ and $R^{16}$ may further have a substituent. Examples of the substituent include the above-described substituents that the alkyl groups represented by $R^{15}$, $R^{16}$, and $R^{17}$ may have.

In the general formula (C-2), from the viewpoint of miscibility between the polyester having a naphthalene structure and the compound having a structure represented by the general formula (C-2), $R^{15}$ and $R^{16}$ are preferably an alkoxy group or an aryloxy group, and $R^{17}$ is preferably an alkyl group or an aryl group.

In the compound having a structure represented by the general formula (C-2), the above-described di- or higher valent group serving as a linking group may be, in the substituent that the alkyl groups represented by $R^{15}$, $R^{16}$, and $R^{17}$ described above can have, a di- or higher valent group provided by removing one or more hydrogen atoms or a group that is a combination of two or more of such groups (note that removing a single hydrogen atom from a substituent provides a divalent group, or removing two hydrogen atoms provides a trivalent group). The di- or higher valent group is preferably di- to hexa-valent group, more preferably a di- to tetra-valent group. The di- or higher valent group is preferably an organic group.

The di- or higher valent group may further have a substituent. Examples of the substituent include the above-described substituents that the alkyl groups represented by $R^{15}$, $R^{16}$, and $R^{17}$ may have.

The di- or higher valent group preferably has a molecular weight of 10 to 1,000.

Of the above-described di- or higher valent groups and a single bond, preferred include a single bond and di- or higher valent groups provided by removing one or more hydrogen atoms from an amino group, an alkyl group, an aryl group, a bis-aryl group (arylaryl group), an arylalkylaryl group, an aryloxyaryl group, an alkoxyalkyl group, an alkoxyaryl group, or an alkylaryl group.

When the compound having a structure represented by the general formula (C-2) is a compound in which a plurality of structures represented by the general formula (C-2) are present in a single molecule, the single molecule has preferably 2 or more and 20 or less phosphorus atoms, more preferably 2 or more and 10 or less phosphorus atoms, still more preferably 2 or more and 5 or less phosphorus atoms.

The following are specific examples of the compound having a structure represented by the general formula (C-2). However, the present invention is not limited to these.

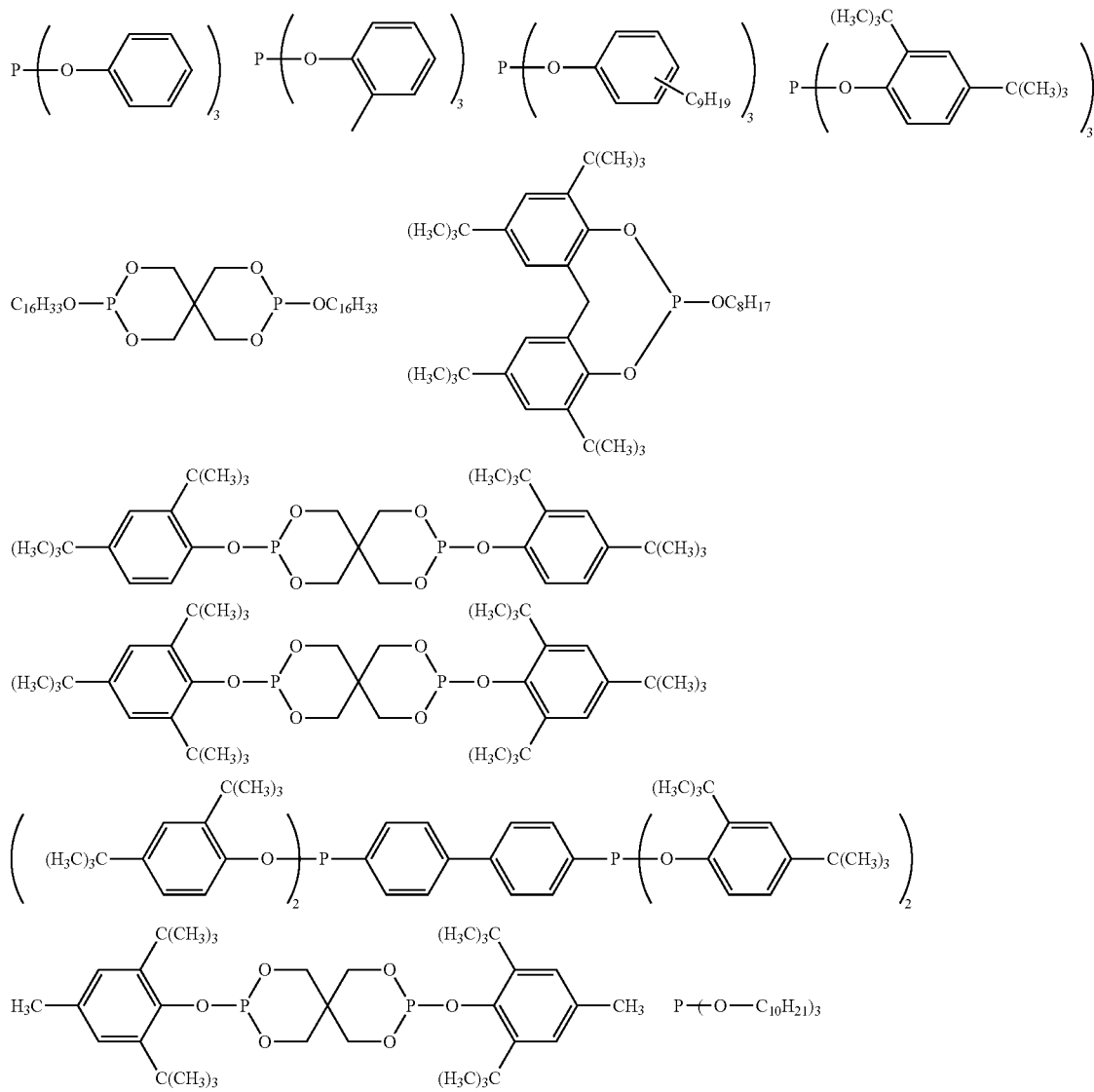

-continued

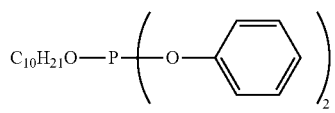
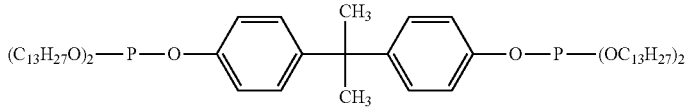
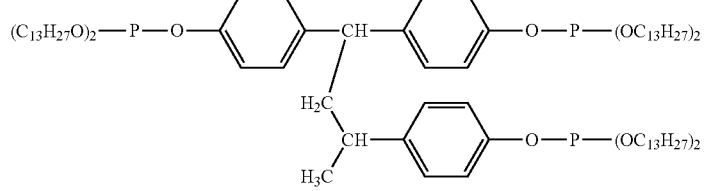
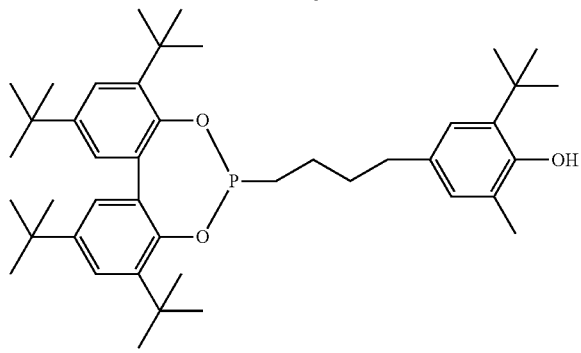
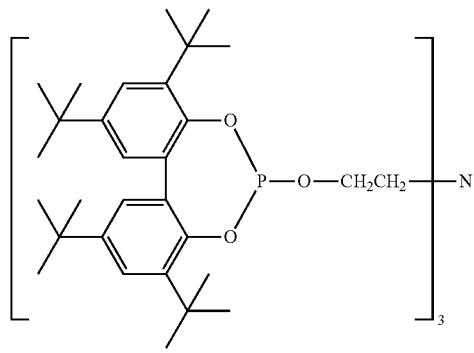

1-17

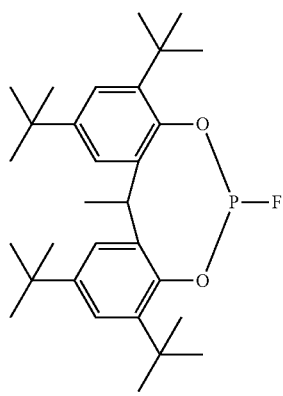
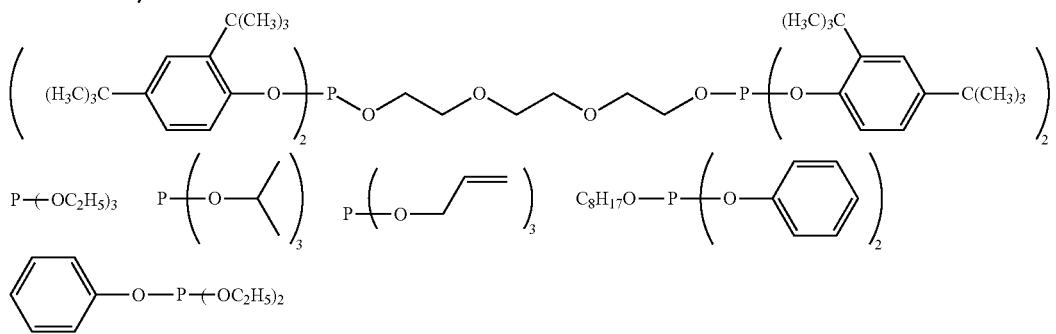
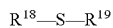
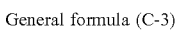

Note that, as the compound having a structure represented by the general formula (C-2), the phosphorous acid ester compounds described in JP2011-527357A can also be suitably employed.

$$R^{18}\text{—S—}R^{19} \qquad \text{General formula (C-3)}$$

In the general formula (C-3), $R^{18}$ and $R^{19}$ represent an alkyl group. $R^{18}$ and $R^{19}$ may be linked together via a di- or higher valent group or a single bond.

In the present invention, the compound having a structure represented by the general formula (C-3) includes, in addition to the compound represented by the general formula (C-3), the following compounds (c) and (d).

(c) a compound having a structure in which a monovalent group provided by removing, from $R^{18}$ or $R^{19}$, a single hydrogen atom is linked to, via a di- or higher valent group or a single bond, at least one of $R^{18}$ or $R^{19}$ of one or more (preferably an integer of 1 to 3) other compounds represented by the general formula (C-3), and (d) a compound having a structure in which a di- or higher valent group provided by removing, from at least one group selected from the group consisting of $R^{18}$ and $R^{19}$, two or more hydrogen atoms in total (for example, removing two hydrogen atoms provides a divalent group, or removing three hydrogen atoms provides a trivalent group), is linked to, via a di- or higher valent group or a single bond, at least one of $R^{18}$ or $R^{19}$ of one or more (preferably an integer of 1 to 3) other compounds represented by the general formula (2).

In other words, in the present invention, the compound having a structure represented by the general formula (C-3) is defined to include the compound represented by the general formula (C-3) and the compound having a structure in which, in a single molecule, a plurality of structures represented by the general formula (C-3) are present.

The alkyl groups represented by $R^{18}$ and $R^{19}$ represent linear, branched, or cyclic, substituted or unsubstituted alkyl groups. They preferably have 1 to 50 carbon atoms, more preferably 2 to 30 carbon atoms, particularly preferably 2 to 20 carbon atoms. Preferred examples include methyl, ethyl, n-propyl, isopropyl, cyclopropyl, butyl, isobutyl, t-butyl, s-butyl, pentyl, isopentyl, neopentyl, t-pentyl, hexyl, cyclohexyl, heptyl, cyclopentyl, octyl, 2-ethylhexyl, nonyl, decyl, dodecyl, tetradecyl, hexadecyl, octadecyl, eicosyl, docosyl, and triacontyl. More preferred include methyl, ethyl, n-propyl, isopropyl, butyl, isobutyl, t-butyl, s-butyl, pentyl, isopentyl, neopentyl, hexyl, cyclohexyl, octyl, 2-ethylhexyl, dodecyl, hexadecyl, and octadecyl, and particularly preferred include methyl, ethyl, n-propyl, isopropyl, butyl, t-butyl, pentyl, isopentyl, hexyl, cyclohexyl, octyl, 2-ethylhexyl, dodecyl, hexadecyl, and octadecyl.

Examples of the substituents of the substituted alkyl groups represented by $R^{18}$ and $R^{19}$ include, in the above-described general formula (C-2), the substituents that the alkyl groups represented by $R^{15}$, $R^{16}$, and $R^{17}$ may have.

Of the substituted alkyl groups represented by $R^{18}$ and $R^{19}$, alkoxycarbonylalkyl groups are preferred. In such an alkoxycarbonylalkyl group, for the number of carbon atoms of the alkoxycarbonyl group, it preferably has 2 to 50 carbon atoms, more preferably 5 to 30 carbon atoms, particularly preferably 9 to 20 carbon atoms.

In the compound having a structure represented by the general formula (C-3), as the di- or higher valent group serving as the linking group, the above-described di- or higher valent group serving as the linking group described in the general formula (C-2) is applicable; the same applies to preferred examples.

The following are specific examples of the compound having a structure represented by the general formula (C-3). However, the present invention is not limited to these.

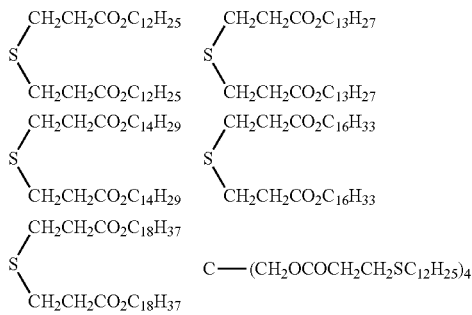

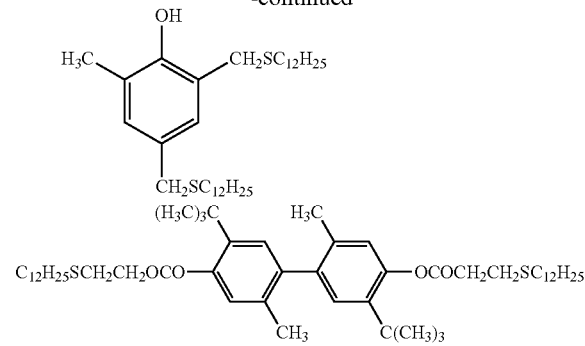

Component (D)

The component (D) is a filler.

The filler may be, for example, a pigment or a clay mineral, and is preferably a pigment.

Examples of the pigment include titanium dioxide, zinc flower, iron oxide red, chromium oxide, iron black, cobalt blue, alumina white, yellow iron oxide, viridian, zinc sulfide, lithopone, cadmium yellow, vermillion, cadmium red, chrome yellow, molybdate orange, zinc chromate, strontium chromate, white carbon, ultramarine, precipitated barium sulfate, calcium carbonate, white lead, Prussian blue, Pigment violet, and carbon black. Of these, carbon black is preferred because it has high dispersibility in the polyester having a naphthalene structure, to provide a flexible tube having further improved peeling resistance and further improved sterilization resistance.

Examples of the clay mineral include talc, pyrophyllite, smectite (such as saponite, hectorite, sauconite, stevensite, montmorillonite, beidellite, and nontronite), vermiculite, mica (such as phlogopite, biotite, zinnwaldite, muscovite, paragonite, celadonite, and glauconite), chlorite (such as clinochlore, chamosite, nimite, pennantite, sudoite, and donbassite), brittle mica (such as clintonite and margarite), surite, serpentine (such as antigorite, lizardite, chrysotile, amesite, cronstedtite, berthierine, greenalite, and garnierite), and kaolin (kaolinite, dickite, nacrite, and halloysite).

For the components (A) to (D), components may be used alone or in combination of two or more thereof. The components (A) to (D) may be, for example, commercially available products and specific examples include commercially available products used in Examples.

In the cover layer, the content of the component (B) is, by mass, 0.15 times or more and 1.50 times or less, preferably 0.20 times or more and 1.50 times or less, the content of the component (A). On the other hand, the total of the contents of the components (C) and (D) is, by mass, 0.010 times or more and 0.50 times or less the content of the component (A).

In the cover layer, the content of the component (B) relative to 100 parts by mass of the polyester having a naphthalene structure is preferably 0.01 to 3 parts by mass, more preferably 0.03 to 2 parts by mass, still more preferably 0.2 to 1 part by mass.

The content of the component (A) is, from the viewpoint of providing a flexible tube having further improved peeling resistance and further improved sterilization resistance, relative to 100 parts by mass of the polyester having a naphthalene structure, preferably 0.1 to 5 parts by mass, more preferably 0.2 to 2 parts by mass, still more preferably 0.4 to 1.2 parts by mass. When the content is in such a preferred range, the action of hydrogen bonds and the like between "—N—R⁵" of the component (A) present in the topcoat-layer-near region of the cover layer and the topcoat layer is effectively exhibited, so that the cover layer is strongly bonded to the topcoat layer inferentially.

From the viewpoint of the peeling resistance and the sterilization resistance of the flexible tube, in the cover layer, the ratio of the content of the component (B) to the total of the contents of the components (C) and (D) (content of component (B)/[total of contents of components (C) and (D)]) is not particularly limited, and is preferably 0.8 or more and 75 or less, more preferably 3 or more and 65 or less, more preferably 5 or more and 60 or less, more preferably 10 or more and 55 or less, still more preferably 15 or more and 50 or less.

In the cover layer, the total of the contents of the components (C) and (D) relative to 100 parts by mass of the polyester having a naphthalene structure is preferably 0.001 to 1 part by mass, more preferably 0.005 to 0.5 parts by mass, still more preferably 0.01 to 0.03 parts by mass.

Polyester Having Naphthalene Structure

Examples of the polyester having a naphthalene structure include a polyester resin having a naphthalene structure and a polyester elastomer having a naphthalene structure.

The polyester having a naphthalene structure is preferably a polyester constituted by a dicarboxylic acid component including a naphthalenedicarboxylic acid component and a diol component.

A specific example of the dicarboxylic acid component preferred as the naphthalenedicarboxylic acid component is 2,6-naphthalenedicarboxylic acid component.

First, the polyester resin having a naphthalene structure will be described.

The polyester resin having a naphthalene structure preferably has a naphthalenedicarboxylic acid component. The polyester resin having a naphthalenedicarboxylic acid component may have, as a dicarboxylic acid component, a dicarboxylic acid component other than the naphthalenedicarboxylic acid component.

The dicarboxylic acid component other than the naphthalenedicarboxylic acid component is not particularly limited and those ordinarily used as dicarboxylic acid components constituting polyester resins are widely applicable. Examples include constituent components derived from terephthalic acid, isophthalic acid, phthalic acid (ortho form), sodium 5-sulfoisophthalate, oxalic acid, succinic acid, adipic acid, sebacic acid, azelaic acid, dodecanedioic acid, dimer acid, maleic acid, fumaric acid, itaconic acid, citraconic acid, mesaconic acid, or cyclohexanedicarboxylic acid, for example. Such dicarboxylic acid components may be used alone or in combination of two or more thereof.

For the polyester resin having a naphthalene structure, those ordinarily used as diol components constituting polyester resins are widely applicable. Examples include constituent components derived from ethylene glycol, diethylene glycol, 1,3-propanediol, 1,4-butanediol, neopentyl glycol, 1,6-hexanediol, cyclohexanedimethanol, triethylene glycol, bisphenol A, or bisphenol S, for example. Such diol components may be used alone or in combination of two or more thereof.

The polyester resin having a naphthalene structure may have a hydroxycarboxylic acid component as a constituent component. Examples of the hydroxycarboxylic acid component include constituent components derived from ε-caprolactone, lactic acid, or 4-hydroxybenzoic acid, for example. These hydroxycarboxylic acid components may be used alone or in combination of two or more thereof.

The polyester resin having a naphthalene structure may be a homopolymer or copolymer constituted by the above-described components and may further contain a small amount of trifunctional compound component such as trimellitic acid, trimesic acid, pyromellitic acid, trimethylolpropane, glycerol, or pentaerythritol.

As such polyester resins having a naphthalene structure, two or more homopolymers or copolymers constituted by the above-described components may be used in combination.

Next, the polyester elastomer having a naphthalene structure will be described.

The polyester elastomer having a naphthalene structure preferably has a naphthalenedicarboxylic acid component. More preferred is a copolymer constituted by a hard segment formed of a crystalline polyester chain including a dicarboxylic acid component including a naphthalenedicarboxylic acid component and a low-molecular-weight diol component as constituent components, and at least any one soft segment of the following (i) to (iii):

(i) a soft segment constituted by an aliphatic polyester chain, (ii) a soft segment constituted by an aliphatic polymer diol component, and (iii) a soft segment constituted by a polyester chain constituted by an aliphatic polymer diol component and a dicarboxylic acid component including an aromatic dicarboxylic acid.

In other words, the naphthalene structure may be introduced into any one of or both of the hard segment and the soft segment, and is preferably at least introduced into the hard segment.

A specific example of the dicarboxylic acid component preferred as the naphthalenedicarboxylic acid component is 2,6-naphthalenedicarboxylic acid component. Hereinafter, a polyester elastomer in which the hard segment has a naphthalene structure will be described.

For a polyester elastomer in which the hard segment has a naphthalene structure, the hard segment preferably has a naphthalenedicarboxylic acid component. When the hard segment has a naphthalenedicarboxylic acid component, all the dicarboxylic acid components of the hard segment may be naphthalenedicarboxylic acid components, or the hard segment may have a dicarboxylic acid component other than naphthalenedicarboxylic acid components. As the dicarboxylic acid component other than naphthalenedicarboxylic acid components that constitutes the hard segment, those ordinarily used as dicarboxylic acid components constituting hard segments of ordinary polyester elastomers are widely applicable. Examples include the dicarboxylic acid components other than naphthalenedicarboxylic acid components having been described in the description of the polyester resin having a naphthalene structure; it can have one or two or more of such dicarboxylic acid components. In particular, the dicarboxylic acid component other than naphthalenedicarboxylic acid components that constitutes the hard segment preferably includes an aromatic dicarboxylic acid component (dicarboxylic acid component having an aromatic ring); preferably 50 mass % or more (preferably 70 mass % or more, more preferably 80 mass % or more, still more preferably 90 mass % or more) of the dicarboxylic acid component other than naphthalenedicarboxylic acid components is an aromatic dicarboxylic acid component. The dicarboxylic acid component other than naphthalenedicarboxylic acid components that constitutes the hard segment is also preferably entirely an aromatic dicarboxylic acid component.

As the diol component constituting the hard segment, those ordinarily used as diol components constituting polyester resins are widely applicable. Examples include the diol components having been described in the polyester resin having a naphthalene structure; it may have one or two or more of such diol components.

The hard segment may have one or two or more hydroxycarboxylic acid components having been described in the description of the polyester resin having a naphthalene structure, as constituent components.

The hard segment may be a homopolymer or copolymer constituted by the above-described constituent components.

When the soft segment is the (i) aliphatic polyester chain, the dicarboxylic acid component constituting the aliphatic polyester chain is not particularly limited as long as it is an aliphatic dicarboxylic acid component. For example, it can have a constituent component derived from oxalic acid, succinic acid, adipic acid, sebacic acid, azelaic acid, dodecanedioic acid, dimer acid, maleic acid, fumaric acid, itaconic acid, citraconic acid, mesaconic acid, or cyclohexanedicarboxylic acid, for example. The aliphatic polyester chain can have one or two or more of these dicarboxylic acid components.

The diol component of the aliphatic polyester chain constituting the soft segment is not particularly limited as long as it is an aliphatic diol component. Examples include aliphatic diol components derived from ethylene glycol, diethylene glycol, triethylene glycol, propylene glycol, dipropylene glycol, 3-methyl-1,5-pentanediol, 1,3-propanediol, 1,4-butanediol, 1,9-nonanediol, neopentyl glycol, 1,5-pentanediol, 1,6-hexanediol, decamethylene glycol, or cyclohexanedimethanol, for example. It can have one or two or more of these diol components. The aliphatic polyester chain also preferably has, as a diol component, an aliphatic polymer diol component. Examples of the aliphatic polymer diol component include polyalkylene glycols such as polyethylene glycol, polypropylene glycol, and polytetramethylene ether glycol; it can have one or two or more of these aliphatic polymer diol components. In the present invention, the polyalkylene glycol is a compound represented by $HO-[(CH_2)_m O]_n-H$. Here, m is preferably 1 to 12, more preferably 2 to 10, still more preferably 2 to 8, yet more preferably 2 to 6. n is preferably 5 to 100, more preferably 10 to 50.

Alternatively, when the soft segment is the (ii) noncrystalline soft segment derived from an aliphatic polymer diol, this aliphatic polymer diol is not particularly limited as long as it is an aliphatic polymer diol. Examples include polyalkylene glycols such as polyethylene glycol, polypropylene glycol, and polytetramethylene ether glycol. The polyester elastomer can have a structure having, as a soft segment, an aliphatic polymer diol component derived from one or two or more of these. The structure of the polyalkylene glycol has been described above.

Alternatively, when the soft segment is the (iii) soft segment constituted by a polyester chain constituted by an aliphatic polymer diol component and a dicarboxylic acid component including an aromatic dicarboxylic acid, this aliphatic polymer diol component is not particularly limited and may be, for example, the constituent component derived from an aliphatic polymer diol having been described in (ii). The aromatic dicarboxylic acid component may be a constituent component derived from naphthalene dicarboxylic acid. In the case of including the dicarboxylic acid component other than aromatic dicarboxylic acid components, this dicarboxylic acid component may be dicarboxylic acid components having been described in (i).

Examples of the polyester having a naphthalene structure that is commercially available include TQB type (manufactured by Teijin Chemicals Ltd.) and PELPRENE EN type (manufactured by TOYOBO CO., LTD.).

Such polyesters having a naphthalene structure may be used alone or may be used in combination of two or more thereof.

In the case of the cover layer being a single layer, the content of the polyester having a naphthalene structure in the cover layer or, in the case of the cover layer being a plurality of layers, the content of the polyester having a naphthalene structure in the outermost layer is preferably 50 mass % or more, more preferably 60 mass % or more, still more preferably 70 mass % or more, yet more preferably 80 mass % or more, still yet more preferably 90 mass % or more. In the case of the cover layer being a single layer, the cover layer may be a layer formed of the polyester having a naphthalene structure; in the case of the cover layer being a plurality of layers, the outermost layer may be a layer formed of the polyester having a naphthalene structure.

When, in the case of the cover layer being a single layer, the cover layer or, in the case of the cover layer being a plurality of layers, the outermost layer is a blend of the polyester having a naphthalene structure and a polymer other than the polyester having a naphthalene structure, as this polymer, those ordinarily used as covering materials constituting endoscopic flexible tubes are widely applicable. Examples of the polymer include polyesters not having naphthalene structures, polyurethanes, and polyamides.

In the case of the cover layer being a plurality of layers, layers other than the outermost layer also preferably include the polyester having a naphthalene structure.

Each of the polymers usable in a cover layer according to the present invention preferably has a molecular weight of 20,000 to 300,000, more preferably a molecular weight of 50,000 to 200,000, still more preferably a molecular weight of 75,000 to 150,000.

In the present invention, the molecular weight of the polymer constituting the cover layer means the weight-average molecular weight unless otherwise specified. The weight-average molecular weight can be measured, by gel permeation chromatography (GPC), as the polystyrene-equivalent molecular weight. The following are specific measurement conditions.

The measurement can be performed by gel permeation chromatography using a GPC apparatus HLC-8220 (trade name, manufactured by Tosoh Corporation), using chloroform as the eluant and G3000HXL+G2000HXL (both are trade names, manufactured by Tosoh Corporation) as columns, at 23° C., at a flow rate of 1 mL/min, using an RI (differential refractive index) detector for detection.

In this Specification, the number-average molecular weight can be measured under the same conditions as the conditions for the weight-average molecular weight. In this Specification, when a numerical range of the weight-average molecular weight of a compound is described, this numerical range is also a preferred numerical range of the number-average molecular weight of the compound.

The cover layer can be formed so as to contain appropriately various additives ordinarily used as long as advantages of the present invention are not impaired. Examples the additives include a heat-resistance stabilizer, an impact resistance improver, a plasticizer, a lubricant, a metallic soap, and a light-fast auxiliary agent. In the cover layer, the contents of the additives can also be appropriately adjusted. Such additives may be derived from materials of the polyester having a naphthalene structure or may alternatively be added as additives other than the polyester having a naphthalene structure.

Method for Producing Endoscopic Flexible Tube

An endoscopic flexible tube according to the present invention, except for the feature of the cover layer, can be produced by standard procedures. For example, with reference to JP2014-188217A, JP2015-16261A, and JP2016-209649A, an endoscopic flexible tube according to the present invention can be produced.

Endoscopic Medical Apparatus

An endoscopic flexible tube according to the present invention is not limited to endoscopic applications and is widely applicable to endoscopic medical apparatuses. For example, it is also applicable to an endoscope having a distal end equipped with a clip or a wire or an instrument equipped with a basket or a brush, to provide the considerable advantages. Note that the endoscopic medical apparatus is defined to broadly include, in addition to medical apparatuses having the above-described endoscopes as basic structures, medical or medical treatment apparatuses that have flexibility and are introduced into and used within the body, such as remote medical apparatuses.

A preferred embodiment of an endoscopic medical apparatus according to the present invention will be described with reference to an electronic endoscope serving as an example. The electronic endoscope in which an endoscopic flexible tube is incorporated is widely used as a medical apparatus. In the example illustrated in FIG. 1, an electronic endoscope 2 includes an insertion section 3 to be inserted into the body cavity, a main-body operation section 5 coupled to the base-end portion of the insertion section 3, and a universal cord 6 connected to a processor device and a light source device. The insertion section 3 is constituted by a flexible tube 3*a* coupled to the main-body operation section 5, an angle portion 3*b* coupled to the flexible tube 3*a*, and a distal-end portion 3*c* coupled to the distal end of the angle portion 3*b* and including therein an image pick-up device (not shown) for imaging the inside of the body cavity. The flexible tube 3*a*, which accounts for most of the length of the insertion section 3, has flexibility substantially over the whole length; in particular, the portion inserted into inner regions such as the body cavity has a more flexible structure.

The embodiment has been described with reference to, as an example, the electronic endoscope using the image pick-up device to capture an image of the state of the subject, the image being used for observation; however, the present invention is not limited to this and is also applicable to endoscopes employing an optical image guide and used for observing the state of the subject.

Flexible Tube

The flexible tube 3*a* (endoscopic flexible tube) has, as illustrated in FIG. 2, a configuration having a flexible-tube base 14 in which a spiral tube 11, which is disposed on the innermost side and formed by spirally winding a metal strip 11*a*, is covered with a sleeve-shaped mesh body 12 formed by knitting metal wires, and both ends are fitted with metal caps 13, the flexible-tube base 14 having an outer periphery surface covered with a cover layer 15. The spiral tube 11 is drawn as a single layer alone, but may alternatively have a configuration of a coaxial double layer. Note that the cover layer 15 is, in order to clearly illustrate the layer structure, drawn thickly relative to the diameter of the flexible-tube base 14.

In this embodiment, the cover layer 15 is formed so as to have a thickness that is substantially uniform in the longitudinal direction (axial direction) of the flexible-tube base 14. The cover layer 15 has a thickness of, for example, 0.1 to 0.6 mm; the flexible tube 3*a* has an outer diameter D of, for example, 2.0 to 10.0 mm, preferably 3.0 to 8.0 mm. The flexible-tube base 14 has an outer diameter of, for example, 1.6 to 9.6 mm, preferably 2.2 to 7.8 mm. In the case where the insertion section 3 is inserted into the bronchus, the cover layer 15 preferably has a thickness of 0.1 to 0.3 mm, the flexible tube 3*a* preferably has an outer diameter D of 3.0 to 5.0 mm, and the flexible-tube base 14 preferably has an outer diameter of 2.4 to 4.8 mm.

Endoscopic-Flexible-Tube-Base-Covering Material

A flexible tube according to the present invention is preferably produced using an endoscopic-flexible-tube-base-covering material according to the present invention. An endoscopic-flexible-tube-base-covering material according to the present invention includes the component (A), the component (B), at least one of the component (C) or the component (D), and the above-described polyester having a naphthalene structure, wherein, of the materials, the content of the component (B) is, by mass, 0.15 times or more and 1.50 times or less the content of the component (A) and, of the materials, the total of the contents of the components (C) and (D) is, by mass, 0.010 times or more and 0.50 times or less the content of the component (A).

The preparation of an endoscopic-flexible-tube-base-covering material according to the present invention can be itself performed by standard procedures. Note that the contents of the components (solid components) of an endoscopic-flexible-tube-base-covering material according to the present invention are the same as in a flexible tube according to the present invention.

EXAMPLES

Hereinafter, the present invention will be described with reference to Examples further in detail; however, the present invention is not construed so as to be limited to these.

Preparation of cover-layer-forming material

Components in amounts (parts by mass) described in Tables 1-1-1 to 1-2-2 below (hereafter, Tables 1-1-1 to 1-2-2 will be collectively referred to as Table 1) were subjected to, using a twin-screw kneader (product name: KZW15-30MG) manufactured by TECHNOVEL CORPORATION, a melt-kneading treatment at a barrel setting temperature of 270° C. at a number of rotations of the screw of 100 rpm, and the ejected strand being melted was cooled in a water tank and subsequently turned into pellets using a pelletizer. In this way, a cover-layer-forming material (endoscopic-flexible-tube-base-covering material, pellets) having a composition in Table 1 below was obtained.

Production of Polyester Sheet

The pellets obtained above were, with MINI TEST PRESS (manufactured by Toyo Seiki Seisaku-sho, Ltd.), heated at 270° C. and pressed at 10 MPa for 30 seconds, to produce a polyester sheet having a thickness of 0.01 mm and sides of 10 cm.

Production of Topcoat-Layer-Equipped Polyester Sheet

OBBLIGATO SS0068 base agent (coating agent including fluororesin, trade name, manufactured by AGC COAT-TECH Co., Ltd.) and OBBLIGATO SS0068 curing agent (curing agent including polyisocyanate, trade name, manufactured by AGC COAT-TECH Co., Ltd.) were mixed together in base agent:curing agent=2:1 (mass ratio), and applied, using a doctor blade having a thickness of 100 μm, to the polyester sheet produced above. This sheet was left at rest at room temperature (25° C.) for 4 hours and subsequently left at rest at 80° C. for 10 hours to cause a reaction between the base agent and the curing agent, to produce a topcoat-layer-equipped polyester sheet. The topcoat layer was found to have a thickness of 0.02 mm.

Test Example 1 (Evaluation of Peeling Resistance)

The topcoat-layer-equipped polyester sheet produced above was subjected to, using a thermal shock chamber (TSD-101-W (trade name) manufactured by ESPEC CORP.), a heating-cooling treatment constituted by the following steps (1) and (2), defined as a 1 cycle, and cycled for 1,000 cycles.
(1) heating to 60° C. and subsequent holding at 60° C. for 1 hour and 30 minutes
(2) cooling to 25° C. and holding for 1 hour and 30 minutes The topcoat-layer-equipped polyester sheet having been subjected to the heating-cooling treatment (test sheet) was fixed, using an adhesive tape 1 (manufactured by 3M Company, model: 850, length: 10 cm, width: 1.5 cm), on a stage on which the test sheet was placed. To a 5-mm-width peripheral inside region of the test sheet (region extending, for 5 mm, from the edge of each side toward the inside), the adhesive tape 1 was attached and this test sheet was stuck to the stage and fixed. To the topcoat layer, an adhesive tape 2 (manufactured by 3M Company, model: 850, length: 5 cm, width: 1.5 cm) was attached so as not to overlie the adhesive tape 1, and subsequently the adhesive tape 2 was peeled at 120°. The test sheet from which the adhesive tape 2 has been peeled was visually inspected to determine whether or not peeling occurred between the polyester sheet and the topcoat layer. The test was performed for 100 test sheets and the number of test sheets in which peeling was observed was evaluated into the following evaluation grades. S, A, and B are pass grades of this test.

Evaluation Grades
S: 0 sheets
A: 1 to 10 sheets
B: 11 to 20 sheets
C: 20 to 100 sheets Test Example 2 (Evaluation of Sterilization Resistance)

A polyester sheet (without the topcoat layer) produced above was placed into a glass case having a length of 20 cm, a width of 20 cm, and a thickness of 1 cm. The glass case into which the polyester sheet was placed was placed in the channel of an ozonated water generator (trade name, "OWM-10L10P" manufactured by EcoDesign, Inc.) and treated by flowing ozonated water having an ozone concentration of 3 ppm at a flow rate of 1 L/min for 3 hours. From the glass case, the polyester sheet was taken out, washed with distilled water, dried at 23° C.×50% RH (relative humidity) for 24 hours, subsequently subjected to a tensile test using a TENSILON Universal Material Testing Instrument (trade name: RTF-1210, manufactured by A&D Company, Limited), and evaluated into the following evaluation grades (a percentage elongation of 100% means elongation by two times). The results will be described in Table 1 below. S, A, and B are pass grades of this test.

Evaluation Grades
S: breakage did not occur even when the percentage elongation reached 200%
A: breakage did not occur even when the percentage elongation reached 150%, but breakage occurred before the percentage elongation reached 200%
B: breakage did not occur even when the percentage elongation reached 100%, but breakage occurred before the percentage elongation reached 150%
C: breakage occurred before the percentage elongation reached 100%

TABLE 1-1-1

|  | E 1 | E 2 | E 3 | E 4 | E 5 | E 6 | E 7 | E 8 | E 9 | E 10 |
|---|---|---|---|---|---|---|---|---|---|---|
| Polyester-1 | 100 |  | 100 |  | 100 |  | 100 | 100 | 100 | 100 |
| Polyester-2 |  | 100 |  | 100 |  | 100 |  |  |  |  |
| Polyester-3 |  |  |  |  |  |  |  |  |  |  |
| a1 | 1 |  |  |  |  |  |  |  |  |  |
| a2 |  | 1.2 |  |  |  |  |  |  |  |  |
| a3 |  |  | 0.8 |  |  |  |  |  |  |  |
| a4 |  |  |  | 1 |  |  |  |  |  |  |
| a5 |  |  |  |  | 0.3 | 0.5 | 1 | 1 | 0.1 | 0.3 |
| b1 | 0.5 |  |  |  | 0.15 | 0.25 | 0.5 | 0.5 | 0.05 | 0.15 |
| b2 |  | 0.5 |  |  |  |  |  |  |  |  |
| b3 |  |  | 1.2 |  |  |  |  |  |  |  |
| b4 |  |  |  | 0.5 |  |  |  |  |  |  |
| c1 | 0.02 |  |  |  |  |  |  |  |  |  |
| c2 |  | 0.02 |  |  |  | 0.02 |  |  |  |  |
| c3 |  |  | 0.02 |  |  |  |  |  |  |  |
| d1 |  |  |  | 0.02 |  |  | 0.02 |  | 0.002 | 0.006 |
| d2 |  |  |  |  | 0.02 |  |  | 0.02 |  |  |
| Component (B)/Component (A) | 0.50 | 0.42 | 1.50 | 0.50 | 0.50 | 0.50 | 0.50 | 0.50 | 0.50 | 0.50 |
| Components (C) (D)/Component (A) | 0.020 | 0.017 | 0.025 | 0.020 | 0.067 | 0.040 | 0.020 | 0.020 | 0.020 | 0.020 |
| Component (B)/Components (C) (D) | 25.0 | 25.0 | 60.0 | 25.0 | 7.5 | 12.5 | 25.0 | 25.0 | 25.0 | 25.0 |
| Test Example 1 | A | A | A | A | B | A | S | A | A | A |
| Test Example 2 | A | A | A | A | A | A | S | S | B | A |

TABLE 1-1-2

|  | E 11 | E 12 | E 13 | E 14 | E 15 | E 16 | E 17 | E 18 | E 19 |
|---|---|---|---|---|---|---|---|---|---|
| Polyester-1 | 100 | 100 | 100 | 100 | 100 | 100 | 100 | 100 | 100 |
| Polyester-2 | | | | | | | | | |
| Polyester-3 | | | | | | | | | |
| a1 | | | | | | | | | |
| a2 | | | | | | | | | |
| a3 | | | | | | | | | |
| a4 | | | | | | | | | |
| a5 | 1.2 | 1.5 | 3 | 6 | 1 | 1 | 1 | 1 | 1 |
| b1 | 0.6 | 0.75 | 1.5 | 3 | 0.15 | 0.3 | 0.8 | 1.2 | 1.5 |
| b2 | | | | | | | | | |
| b3 | | | | | | | | | |
| b4 | | | | | | | | | |
| c1 | | | | | | | | | |
| c2 | | | | | | | | | |
| c3 | | | | | | | | | |
| d1 | 0.024 | 0.03 | 0.06 | 0.12 | 0.02 | 0.02 | 0.02 | 0.02 | 0.02 |
| d2 | | | | | | | | | |
| Component (B)/Component (A) | 0.50 | 0.50 | 0.50 | 0.50 | 0.15 | 0.30 | 0.80 | 1.20 | 1.50 |
| Components (C) (D)/Component (A) | 0.020 | 0.020 | 0.020 | 0.020 | 0.020 | 0.020 | 0.020 | 0.020 | 0.020 |
| Component (B)/Components (C) (D) | 25.0 | 25.0 | 25.0 | 25.0 | 7.5 | 15.0 | 40.0 | 60.0 | 75.0 |
| Test Example 1 | S | A | A | B | A | S | S | A | A |
| Test Example 2 | A | A | B | B | B | A | A | A | B |

TABLE 1-2-1

|  | E 20 | E 21 | E 22 | E 23 | E 24 | E 25 | E 26 | E 27 | E 28 |
|---|---|---|---|---|---|---|---|---|---|
| Polyester-1 | 100 | 100 | 100 | 100 | 100 | | 100 | | |
| Polyester-2 | | | | | | 100 | | 100 | 100 |
| Polyester-3 | | | | | | | | | |
| a1 | | | | | | | | | |
| a2 | | | | | | | | | |
| a3 | | | | | | | | | |
| a4 | | | | | | | | | 1 |
| a5 | 1 | 1 | 1 | 1 | 1 | 1 | 3 | 5 | |
| b1 | 0.5 | 0.5 | 0.5 | 0.5 | 0.5 | | 0.5 | 1 | |
| b2 | | | | | | 0.22 | | | |
| b3 | | | | | | | | | |
| b4 | | | | | | | | | 0.25 |
| c1 | | | | | | | | | 0.25 |
| c2 | | | | | | | 0.3 | 0.5 | |
| c3 | | | | | | | | | |
| d1 | 0.01 | 0.03 | 0.1 | 0.3 | 0.5 | 0.02 | | | |
| d2 | | | | | | | | | |
| Component (B)/Component (A) | 0.50 | 0.50 | 0.50 | 0.50 | 0.50 | 0.22 | 0.17 | 0.20 | 0.25 |
| Components (C) (D)/Component (A) | 0.010 | 0.030 | 0.100 | 0.300 | 0.500 | 0.020 | 0.100 | 0.100 | 0.250 |
| Component (B)/Components (C) (D) | 50.0 | 16.7 | 5.0 | 1.7 | 1.0 | 11.0 | 1.7 | 2.0 | 4.0 |
| Test Example 1 | S | S | A | B | B | S | B | B | B |
| Test Example 2 | A | A | A | A | B | S | B | B | B |

TABLE 1-2-2

|  | CE 1 | CE 2 | CE 3 | CE 4 | CE 5 | CE 6 | CE 7 | CE 8 | CE 9 |
|---|---|---|---|---|---|---|---|---|---|
| Polyester-1 | 100 | 100 | 100 | 100 | 100 | 100 | 100 | 100 | |
| Polyester-2 | | | | | | | | | |
| Polyester-3 | | | | | | | | | 100 |
| a1 | | 1 | 1 | 1 | 1 | 1 | 1 | | |
| a2 | | | | | | | | 1 | |
| a3 | | | | | | | | 1 | |
| a4 | | | | | | | | | 1 |
| a5 | | | | | | | | | |
| b1 | | 1.6 | 1.6 | 0.2 | 0.1 | 0.4 | 0.3 | | |

TABLE 1-2-2-continued

| | CE 1 | CE 2 | CE 3 | CE 4 | CE 5 | CE 6 | CE 7 | CE 8 | CE 9 |
|---|---|---|---|---|---|---|---|---|---|
| b2 | | | | | | | | | |
| b3 | | | | | | | | | |
| b4 | | | | | | | | | 0.25 |
| c1 | 0.6 | 0.02 | 0.005 | 0.005 | | | | | 0.25 |
| c2 | | | | | | | | | |
| c3 | | | | | | | | | |
| d1 | | | | | 0.005 | 0.55 | 0.02 | 0.02 | |
| d2 | | | | | | | | | |
| Component (B)/Component (A) | 1.60 | 1.60 | 0.20 | 0.10 | 0.40 | 0.30 | | | 0.25 |
| Components (C) (D)/Component (A) | 0.600 | 0.020 | 0.005 | 0.005 | 0.005 | 0.550 | 0.020 | 0.020 | 0.250 |
| Component (B)/Components (C) (D) | 2.7 | 80.0 | 40.0 | 20.0 | 80.0 | 0.5 | | | 1.0 |
| Test Example 1 | B | B | C | C | C | C | C | C | C |
| Test Example 2 | C | C | B | C | C | B | C | C | C |

Descriptions of Terms in Tables

E: Example
CE: Comparative Example

Compounds Used in Examples

Polyester-1:
  Polyester elastomer having naphthalene structure (trade name: PELPRENE EN, manufactured by TOYOBO CO., LTD., weight-average molecular weight: 120,000)
Polyester-2:
  Polyester elastomer having naphthalene structure (trade name: TQB-OT, manufactured by Teijin Chemicals Ltd., weight-average molecular weight: 120,000)
a1:
  Component (A), compound represented by general formula (a-2) (trade name: ADK STAB LA-63P, manufactured by ADEKA CORPORATION)
a2:
  Component (A), compound represented by general formula (a-1) (trade name: TINUVIN 765, manufactured by BASF)
a3:
  Component (A), compound represented by general formula (a-1) (trade name: FLAMESTAB NOR 116, manufactured by BASF)
a4:
  Component (A), compound represented by general formula (a-2) (trade name: CHIMASSORB 2020FDL, manufactured by BASF)
a5:
  Component (A), compound represented by general formula (a-2) (trade name: CHIMASSORB 944FDL, manufactured by BASF)
b1:
  Component (B), compound represented by general formula (b-1) (trade name: IRGANOX 1010, manufactured by BASF)
b2:
  Component (B), compound represented by general formula (b-2) (trade name: SUMILIZER GS, manufactured by Sumitomo Chemical Company, Limited)
b3:
  Component (B), compound represented by general formula (B-2) (trade name: IRGAFOS FS-042, manufactured by Aldrich Corporation)
b4:
  Component (B), compound represented by general formula (B-3) (trade name: IRGANOX HP-136, manufactured by ADEKA CORPORATION)
c1:
  Component (C), compound represented by formula (C-1) (ascorbic acid)
c2:
  Component (C), compound represented by general formula (C-2) (trade name: ADK STAB HP-10, manufactured by ADEKA CORPORATION)
c3:
  Component (C), compound represented by general formula (C-3) (trade name: ADK STAB AO-412S, manufactured by ADEKA CORPORATION)
d1:
  Component (D), carbon black (trade name: DIABLACK, manufactured by Mitsubishi Chemical Corporation)
d2:
  Component (D), talc (trade name: NANO ACE D-1000, manufactured by NIPPON TALC Co., Ltd.)

Compounds Used in Comparative Examples

Polyester-3:
  Polyester elastomer not having naphthalene structure (polyester elastomer having benzene structure, trade name: PELPRENE P-280B, manufactured by TOYOBO CO., LTD.)
"Component (B)/Component (A)": Content of component (B)/Content of component (A) "Components (C) (D)/Component (A)": Total of contents of components (C) and (D)/Content of component (A)
"Component (B)/Components (C) (D)": Content of component (B)/Total of contents of components (C) and (D)

As is clear from Table 1, even in the case of using the component (A), the component (B), at least one of the component (C) or the component (D), and the polyester having a naphthalene structure, when the contents of the components do not satisfy the feature of the present invention, evaluation in terms of at least one of peeling resistance or sterilization resistance has resulted in fail (Comparative Examples 1 to 6).

In addition, even in the case of using the polyester having a naphthalene structure, the component (A), and the component (D) according to the present invention, when the component (B) is not used, evaluation in terms of both of peeling resistance and sterilization resistance has resulted in fail (Comparative Examples 7 and 8).

In addition, even in the case of using the components (A) to (C) according to the present invention, when a polyester not having a naphthalene structure is used, evaluation in terms of both of peeling resistance and sterilization resistance has resulted in fail (Comparative Example 9).

By contrast, Examples according to the present invention are evaluated as having passed in terms of both of peeling resistance and sterilization resistance. In addition, for example, Examples 16 and 17 compared with Examples 19 and 23 have demonstrated that, when "Content of component (B)/[Total of contents of components (C) and (D)]" is within the specific range, both of high peeling resistance and high sterilization resistance can be achieved.

The present invention has been described together with embodiments thereof; however, we do not intend to limit our invention in any minor portion of the descriptions unless otherwise specified; we believe that the invention is construed broadly without departing from the spirit and scope of the invention described in the attached claims.

REFERENCE SIGNS LIST 2 electronic endoscope (endoscope)
3 insertion section
   3a flexible tube
   3b angle portion
   3c distal-end portion
5 main-body operation section
6 universal cord
11 spiral tube
   11a metal strip
12 sleeve-shaped mesh body
13 metal cap
14 flexible-tube base
15 cover layer

What is claimed is:

1. An endoscopic flexible tube comprising: a flexible-tube base containing metal as a constituent material, and a cover layer covering an outer periphery of the flexible-tube base,
wherein the cover layer includes a component (A) below, a component (B) below, at least one of a component (C) below or a component (D) below, and a polyester having a naphthalene structure,
in the cover layer, a content of the component (B) below by mass is 0.15 times or more and 1.50 times or less a content of the component (A) below, and
in the cover layer, a total of contents of the components (C) and (D) below by mass is 0.010 times or more and 0.50 times or less the content of the component (A) below,
component (A): a compound having a structure represented by a general formula (A) below,
component (B): at least one of a compound having a structure represented by a general formula (B-1) below, a compound represented by a general formula (B-2) below, or a compound represented by a general formula (B-3) below,
component (C): at least one of a compound represented by a formula (C-1) below, a compound having a structure represented by a general formula (C-2) below, or a compound having a structure represented by a general formula (C-3) below,
component (D): a filler,

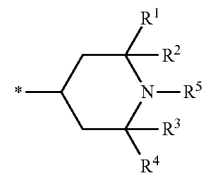

General formula (A)

where $R^1$ to $R^4$ represent a hydrogen atom or an alkyl group having 1 to 12 carbon atoms, $R^5$ represents a hydrogen atom, an alkyl group having 1 to 18 carbon atoms, or $-OR^a$, $R^a$ represents a hydrogen atom or an alkyl group having 1 to 20 carbon atoms, * represents a bonding site for being incorporated into the compound,

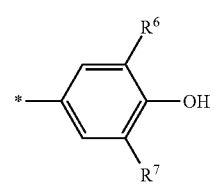

General formula (B-1)

General formula (B-2)

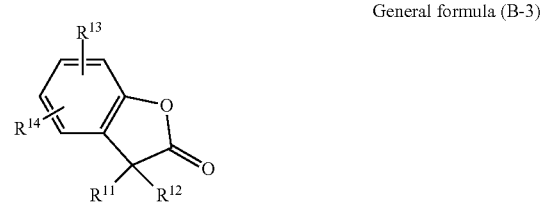

General formula (B-3)

in the general formula (B-1), $R^6$ and $R^7$ represent a hydrogen atom, an alkyl group having 1 to 12 carbon atoms, or an aralkyl group having 7 to 36 carbon atoms, and * represents a bonding site for being incorporated into the compound, in the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group, $R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^8$ and $R^9$, $R^9$ and $R^{10}$, or $R^8$ and $R^{10}$ may be linked together to form a five- to seven-membered ring without forming a 2,2,6,6-tetraalkylpiperidine skeleton, with the proviso that $R^8$ and $R^9$ are not simultaneously hydrogen atoms, and $R^8$ and $R^9$ have 7 or more carbon atoms in total, in the general formula (B-3), $R^{11}$ to $R^{14}$ represent a hydrogen atom, an alkyl group having 1 to 20 carbon atoms, or an aryl group having 6 to 15 carbon atoms, Formula (C-1)

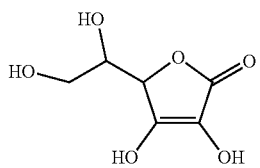

General formula (C-2)

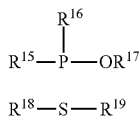

General formula (C-3)

$R^{18}-S-R^{19}$ in the general formula (C-2), $R^{15}$ and $R^{16}$ represent an alkyl group, an aryl group, an alkoxy group, an aryloxy group, or a halogen atom, and $R^{17}$ represents an alkyl group or an aryl group, and in the general formula (C-3), $R^{18}$ and $R^{19}$ represent an alkyl group.

2. The endoscopic flexible tube according to claim 1, wherein the component (A) includes at least one of a compound represented by a general formula (a-1) below or a compound having a constituent component represented by a general formula (a-2) below, General formula (a-1)

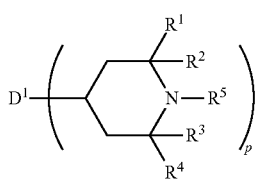

General formula (a-2)

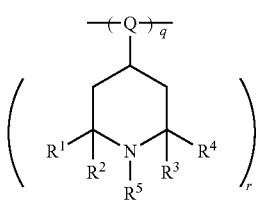

where $R^1$ to $R^5$ respectively have the same definitions as $R^1$ to $R^5$ of the general formula (A), p is an integer of 2 or more, $D^1$ represents a p-valent linking group, q represents a positive integer, Q represents an r+2-valent linking group, and r is 1 or 2.

3. The endoscopic flexible tube according to claim 1, wherein the compound having the structure represented by the general formula (B-1) includes at least one of a compound represented by a general formula (b-1) below or a compound represented by a general formula (b-2) below, General formula (b-1)

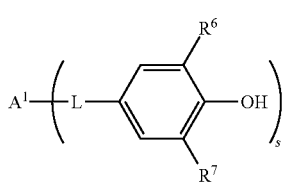

General formula (b-2)

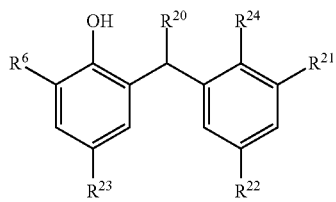

where $R^6$ and $R^7$ respectively have the same definitions as $R^6$ and $R^7$ of the general formula (B-1), L represents a single bond or a divalent linking group, s is an integer of 2 to 4, $A^1$ represents a di- to tetra-valent linking group, $R^{20}$ to $R^{23}$ have the same definitions as $R^6$, and $R^{24}$ represents a reactive organic substituent.

4. The endoscopic flexible tube according to claim 1, wherein the component (D) includes carbon black.

5. The endoscopic flexible tube according to claim 1, comprising a topcoat layer.

6. An endoscopic medical apparatus comprising the endoscopic flexible tube according to claim 1.

7. An endoscopic-flexible-tube-base-covering material comprising: a component (A) below, a component (B) below, at least one of a component (C) below or a component (D) below, and a polyester having a naphthalene structure, wherein, in the material, a content of the component (B) below by mass is 0.15 times or more and 1.50 times or less a content of the component (A) below, and in the material, a total of contents of the components (C) and (D) below by mass is 0.010 times or more and 0.50 times or less the content of the component (A) below, component (A): a compound having a structure represented by a general formula (A) below, component (B): at least one of a compound having a structure represented by a general formula (B-1) below, a compound represented by a general formula (B-2) below, or a compound represented by a general formula (B-3) below, component (C): at least one of a compound represented by a formula (C-1) below, a compound having a structure represented by a general formula (C-2) below, or a compound having a structure represented by a general formula (C-3) below, component (D): a filler, General formula (A)

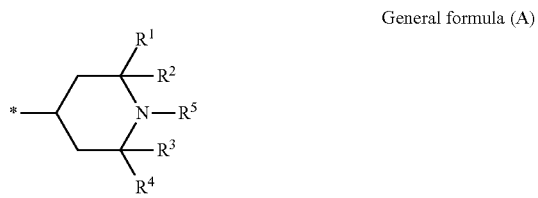

where $R^1$ to $R^4$ represent a hydrogen atom or an alkyl group having 1 to 12 carbon atoms, $R^5$ represents a hydrogen atom, an alkyl group having 1 to 18 carbon atoms, or $-OR^a$, $R^a$ represents a hydrogen atom or an alkyl group having 1 to 20 carbon atoms, and * represents a bonding site for being incorporated into the compound,

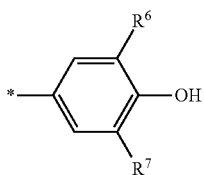

General formula (B-1)

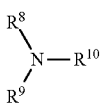

General formula (B-2)

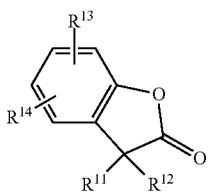

General formula (B-3)

in the general formula (B-1), $R^6$ and $R^7$ represent a hydrogen atom, an alkyl group having 1 to 12 carbon atoms, or an aralkyl group having 7 to 36 carbon atoms, and * represents a bonding site for being incorporated into the compound, in the general formula (B-2), $R^8$ and $R^9$ represent a hydrogen atom, an aliphatic group, an acyl group, an aliphatic oxycarbonyl group, an aromatic oxycarbonyl group, an aliphatic sulfonyl group, or an aromatic sulfonyl group, $R^{10}$ represents an aliphatic group, an aliphatic oxy group, an aromatic oxy group, an aliphatic thio group, an aromatic thio group, an acyloxy group, an aliphatic oxycarbonyloxy group, an aromatic oxycarbonyloxy group, a substituted amino group, a heterocyclic group, or a hydroxy group, $R^8$ and $R^9$, $R^9$ and $R^{10}$, or $R^8$ and $R^{10}$ may be linked together to form a five- to seven-membered ring without forming a 2,2,6,6-tetraalkylpiperidine skeleton, with the proviso that $R^8$ and $R^9$ are not simultaneously hydrogen atoms, and $R^8$ and $R^9$ have 7 or more carbon atoms in total, in the general formula (B-3), $R^{11}$ to $R^{14}$ represent a hydrogen atom, an alkyl group having 1 to 20 carbon atoms, or an aryl group having 6 to 15 carbon atoms,

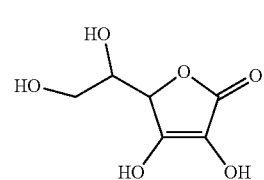

Formula (C-1)

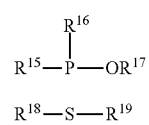

General formula (C-2)

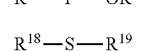

General formula (C-3)

in the general formula (C-2), $R^{15}$ and $R^{16}$ represent an alkyl group, an aryl group, an alkoxy group, an aryloxy group, or a halogen atom, and $R^{17}$ represents an alkyl group or an aryl group, and in the general formula (C-3), $R^{18}$ and $R^{19}$ represent an alkyl group.

* * * * *